US012606790B2

(12) United States Patent
Igarashi

(10) Patent No.: US 12,606,790 B2
(45) Date of Patent: Apr. 21, 2026

(54) CELL CULTURING SYSTEM, SENSOR KIT, AND METHOD OF DETERMINING LIFESPAN OF ENZYME SENSOR

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 737 days.

(21) Appl. No.: 17/864,185

(22) Filed: Jul. 13, 2022

(65) Prior Publication Data

US 2022/0348860 A1 Nov. 3, 2022

Related U.S. Application Data

(63) Continuation of application No. PCT/JP2021/004386, filed on Feb. 5, 2021.

(30) Foreign Application Priority Data

Feb. 10, 2020 (JP) ................................. 2020-020478

(51) Int. Cl.
*C12M 1/00* (2006.01)
*C12M 1/12* (2006.01)
(Continued)

(52) U.S. Cl.
CPC ............ *C12M 41/32* (2013.01); *C12M 25/10* (2013.01); *C12M 29/18* (2013.01); *C12Q 1/006* (2013.01)

(58) Field of Classification Search
CPC ...... C12M 41/32; C12M 25/10; C12M 29/18; C12M 41/48; C12Q 1/006; C12Q 1/005
See application file for complete search history.

(56) References Cited

U.S. PATENT DOCUMENTS 5,082,786 A 1/1992 Nakamoto
2005/0112549 A1 5/2005 Baumgardner et al.
(Continued)

FOREIGN PATENT DOCUMENTS

JP S62-240848 A 10/1987
JP H06-273372 9/1994
(Continued)

OTHER PUBLICATIONS

English machine translation of JP 2010-019569. Translated on Jul. 17, 2025.*

(Continued)

*Primary Examiner* — Liban M Hassan
(74) *Attorney, Agent, or Firm* — Sheridan Ross P.C.

(57) ABSTRACT

A cell culturing system includes an enzyme sensor that detects a concentration of a predetermined component of a culture medium used for culturing of cells, a sensor flow path in which the enzyme sensor is disposed, and a bioreactor that performs culturing of cells while causing the culture medium to flow through the sensor flow path, and further includes a deterioration index calculation unit that determines a deterioration index of the enzyme sensor, based on a detected concentration value of the enzyme sensor, and a detection period during which the detected concentration value is detected, and a lifespan determination unit that detects whether or not an integrated value of the deterioration index has reached a threshold value, and thereby determines the lifespan of the enzyme sensor.

14 Claims, 19 Drawing Sheets

(51) Int. Cl.
  _C12M 1/34_  (2006.01)
  _C12Q 1/00_  (2006.01)

(56)  References Cited

U.S. PATENT DOCUMENTS

2016/0356635 A1* 12/2016 Usami .................... G01D 18/00
2018/0238475 A1* 8/2018 Zumbrum .............. A01N 1/147
2019/0352589 A1 11/2019 Jing et al.

FOREIGN PATENT DOCUMENTS

| JP | H08233770 | A | * | 9/1996 |
|----|-----------|---|---|--------|
| JP | H09-297832 | | | 11/1997 |
| JP | 2002-168860 | | | 6/2002 |
| JP | 2010-019569 | A | | 1/2010 |
| JP | 2010-048623 | | | 3/2010 |
| JP | 2013-053927 | | | 3/2013 |
| JP | 2015151967 | A | * | 8/2015 |
| JP | 2017-143775 | A | | 8/2017 |

OTHER PUBLICATIONS

Rocchitta, Gaia et al. "Enzyme Biosensors for Biomedical Applications: Strategies for Safeguarding Analytical Performances in Biological Fluids" *Sensors* 2016, 16, 780.
International Search Report for International Application No. PCT/JP2021/004386, mailed May 18, 2021.
Written Opinion for International Application No. PCT/JP2021/004386, mailed May 18, 2021.
English Translation of Official Action for Japan Patent Application No. 2022-529618, dated Oct. 29, 2024, 6 pages.
Official Action with Machine Translation for China Patent Application No. 202180013481.8, dated Jan. 4, 2025, 19 pages.
International Preliminary Report on Patentability for International Application No. PCT/JP2021/004386, mailed Aug. 25, 2022.

* cited by examiner

CELL CULTURING SYSTEM, SENSOR KIT, AND METHOD OF DETERMINING LIFESPAN OF ENZYME SENSOR

CROSS REFERENCE TO RELATED APPLICATIONS

The present disclosure is a continuation of and claims benefit to PCT/JP2021/004386 filed on Feb. 5, 2021, entitled "CELL CULTURING SYSTEM, SENSOR KIT, AND METHOD OF DETERMINING LIFESPAN OF ENZYME SENSOR" which claims priority to Japanese Patent Application No. 2020-020478 filed on Feb. 10, 2020. The entire disclosure of the applications listed above are hereby incorporated herein by reference, in their entirety, for all that they teach and for all purposes.

BACKGROUND

The present disclosure relates to a cell culturing system, a sensor kit, and a method of determining the lifespan of an enzyme sensor.

In the practice of regenerative medicine, a treatment is performed in which therapeutic cells (also referred to as biological components) are cultured, and the cultured cells are administered to a patient. For culturing the therapeutic cells, for example, as disclosed in Japanese Patent Publication No. 2017-143775, a cell culturing system has been proposed in which cells are cultured inside of hollow fibers. Such a cell culturing system includes an inner side circulation flow path communicating with the interior of the hollow fibers, and an outer side circulation flow path communicating with the exterior of the hollow fibers. In addition, a liquid (e.g., a culture medium) containing the cells is supplied to the inner side circulation flow path that communicates with the interior of the hollow fibers, and supplying of nutrients and a gas component as well as discharging of metabolites is carried out through a liquid (culture medium) that flows through the outer side circulation flow path that communicates with the exterior of the hollow fibers.

In the cell culturing system, when culturing of cells is carried out, it is preferable that the state of the culture medium flowing through the circulation flow paths and the expansion condition of the cells be managed in real time. The state of the culture medium can be determined by detecting an amount of dissolved oxygen, an amount of dissolved carbon dioxide, a pH, and a glucose concentration (e.g., the energy supplied to the cells). Further, the amount at which the cells are expanded can be determined by measuring a concentration of lactic acid, which is a metabolite of the cells.

SUMMARY

Concerning measurement of the glucose concentration and the lactic acid concentration, from the standpoint of selectivity, an enzyme sensor is used. However, the enzyme that is used in the enzyme sensor tends to be unstable, the lifespan thereof is comparatively short, and cases may occur in which the enzyme sensor reaches the end of its lifespan, and the measurement sensitivity thereof decreases during a period in which the cells are being cultured. Accordingly, a problem arises in that management of the cell culturing process becomes difficult, because it is not known whether the decrease in the measured concentration value during the period in which the cells are being cultured is caused by the state of the culture medium or the expansion amount of the cells, or due to the lifespan of the enzyme sensor.

In Japanese Patent Publication No. 62-240848, in the case that urine or a blood component having a relatively stable substrate concentration is a target of detection, it is disclosed to carry out detection and correction of the sensitivity of an enzyme sensor in accordance with a number of times or a frequency of use of the enzyme sensor.

However, in a cell culturing system in which the glucose concentration and the lactic acid concentration fluctuate greatly between an initial stage and a final stage during culturing of the cells, a problem arises in that the method disclosed in Japanese Patent Publication No. 62-240848 is incapable of sufficiently determining a timing at which a decrease in the sensitivity of the enzyme sensor occurs.

Thus, the present disclosure provides a cell culturing system, a sensor kit, and a method of determining a lifespan of an enzyme sensor, which are capable of determining, even during a period in which cells are being cultured, that an end of the lifespan of the enzyme sensor has been reached.

One aspect of the present disclosure includes a cell culturing system, including an enzyme sensor configured to detect a concentration of a predetermined component of a culture medium used for culturing of cells, a sensor flow path in which the enzyme sensor is disposed, and a bioreactor configured to perform culturing of cells while causing the culture medium to flow through the sensor flow path, and further including a deterioration index calculation unit configured to determine a deterioration index of the enzyme sensor, based on a detected concentration value of the enzyme sensor, and a detection period during which the detected concentration value is detected, and a lifespan determination unit configured to detect whether or not the deterioration index has reached a threshold value, and thereby determine the lifespan of the enzyme sensor.

Another aspect of the present disclosure includes a sensor kit which is used in the above-described cell culturing system, including an enzyme sensor configured to detect a concentration of a predetermined component of a culture medium used for culturing of cells, and a sensor flow path extended from one end and another end of the enzyme sensor, wherein the sensor flow path is made up from a thermoplastic tube which is closed at both ends, and which is capable of being aseptically joined to a flow path through which the culture medium of the cell culturing system flows, and the enzyme sensor is configured to detect the concentration of the predetermined component within the culture medium, and transmit a detected value to the cell culturing system.

Yet another aspect of the present disclosure includes a method of determining a lifespan of an enzyme sensor in a cell culturing system in which cells are cultured while detecting a concentration of a predetermined component of a culture medium using the enzyme sensor, the method including a step of detecting, by a control unit, a detected concentration value of the enzyme sensor, and a detection period during which the detected concentration value is detected, a deterioration index detection step of determining, by a deterioration index calculation unit, a deterioration index of the enzyme sensor, based on the detected concentration value of the enzyme sensor and the detection period, and a lifespan determination step of determining, by a lifespan determination unit, whether or not an integrated value of the deterioration index has reached a threshold value.

According to the cell culturing system, the sensor kit, and the method of determining a lifespan of the enzyme sensor having the above-described aspects, the lifespan of the enzyme sensor can be determined even during a period in which cells are being cultured. Consequently, an appropriate management in the cell culturing system can be performed.

DETAILED DESCRIPTION

Embodiments of the present disclosure will be presented and described in detail below with reference to the accompanying drawings.

Figure 1:
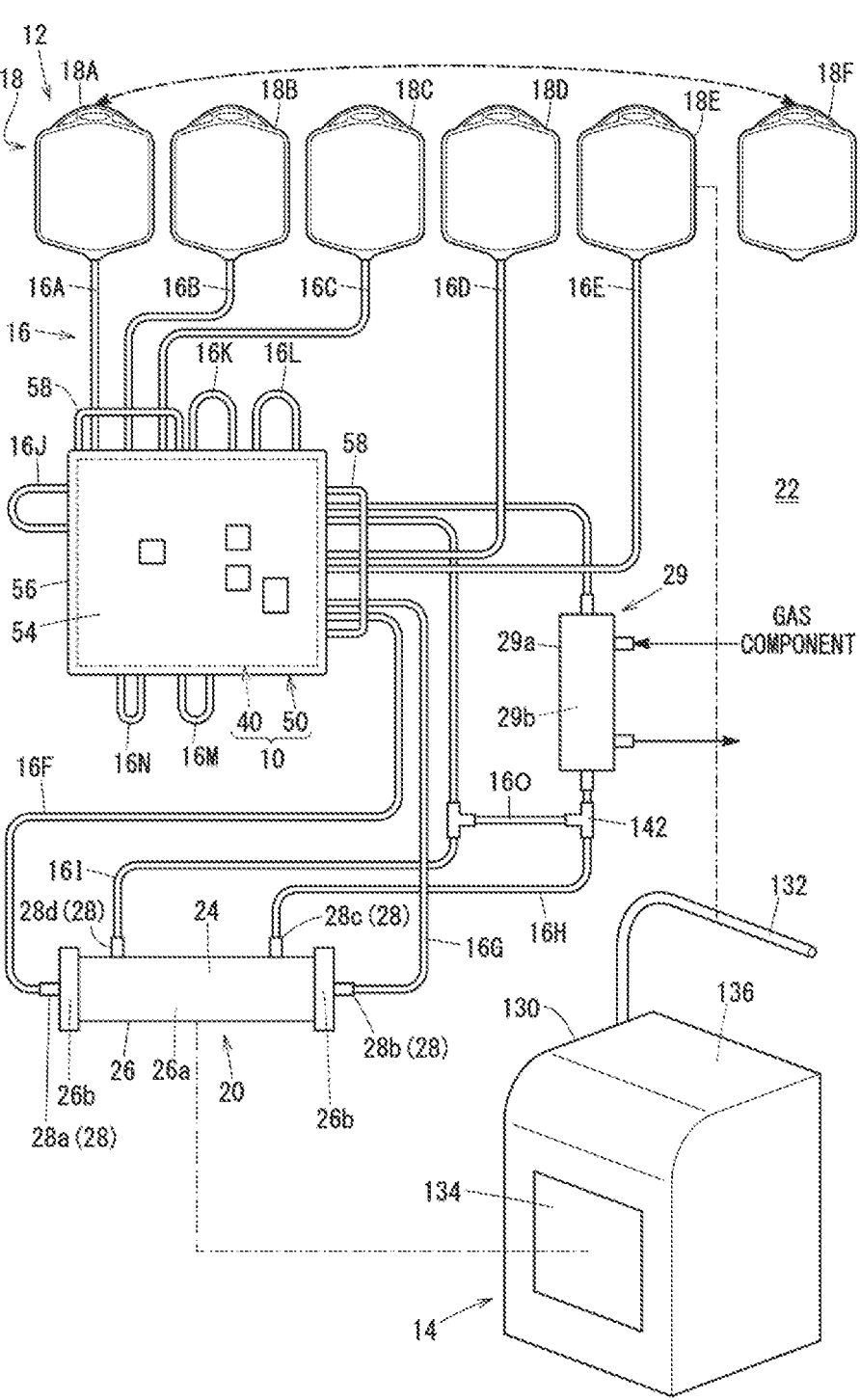
FIG. 1 is schematic diagram showing a cell culturing system according to at least one embodiment of the present disclosure.

As shown in FIG. 1, a cell culturing system 22, according to at least one embodiment of the present disclosure, is equipped with a cell culturing kit 12 in which a liquid containing a biological component and liquids for treating the biological component are capable of flowing, and a cell culturing device 14 in which the cell culturing kit 12 is set. Further, the cell culturing kit 12 includes a flow path cassette 10 in which a plurality of liquid pathways are aggregated, and which is set in the cell culturing device 14.

In addition to the flow path cassette 10, the cell culturing kit 12 comprises, as members that make up the plurality of pathways, a plurality of tubes 16, a plurality of bags 18 (e.g., medical bags), and a bioreactor 20. The cell culturing kit 12 allows a plurality of types of liquids contained in the respective bags 18 to flow through the flow path cassette 10 and through each of the tubes 16 under the operation of the cell culturing device 14, and carries out culturing of cells in the bioreactor 20.

In some embodiments, the cell culturing system 22 performs a culturing treatment for expanding therapeutic cells used in regenerative medicine. Further, the liquids that flow inside the cell culturing kit 12 may be or comprise a solution containing cells (hereinafter referred to as a cell solution), a culture medium (e.g., culturing solution) which is supplied in order to expand the cells, a cleaning solution for cleaning the interior of the cell culturing kit 12, and/or a release solution for releasing the cells. More specifically, in a set state of the cell culturing kit 12, the cell culturing system 22 carries out a culturing process in which the bioreactor 20 is seeded with the cells, and furthermore, the cells are cultured by supplying the culture medium, and thereafter, the expanded cells are released and collected from the bioreactor 20.

The therapeutic cells are not particularly limited, and may include, for example, cells (such as T cells and the like) contained in blood, and stem cells (e.g., ES cells, iPS cells, mesenchymal stem cells, and/or the like). An appropriate culture medium may be selected according to the biological cells, and for example, such a culture medium may include a medium prepared by adding various amino acids, vitamins, serum and the like, to a balanced salt solution (BSS) as a basic solution. Further, the cleaning solution is not particularly limited, and examples thereof may include, but are in no way limited to, buffered solutions such as PBS (Phosphate Buffered Salts), TBS (Tris-Buffered Saline) and/or the like, or physiological saline. Further, as the release solution, for example, trypsin or an EDTA solution can be applied.

Among the plurality of bags 18 of the cell culturing kit 12, there are included a cell solution bag 18A in which the cell solution is accommodated, a cleaning solution bag 18B in which the cleaning solution is accommodated, and a culture medium bag 18C in which the culture medium is accommodated. Furthermore, the cell culturing kit 12 includes empty bags 18 among the plurality of bags 18. Such empty bags 18 include a waste liquid bag 18D into which a liquid that is discarded in the culturing process flows, and a collection bag 18E in which cells (and other liquids) obtained in the culturing process are collected. Further, among the bags 18, a release solution bag 18F in which the release solution is accommodated is separately prepared. During the course of the culturing process, the release solution bag 18F is exchanged by the operator with one of the bags 18 (e.g., the cell solution bag 18A) that has been connected beforehand.

The cell solution bag 18A, the cleaning solution bag 18B, and the culture medium bag 18C, etc., are aseptically joined to ends of the respective tubes 16 using a commercially available aseptic joining device. The tubes 16 are thermoplastic tubes made of a thermoplastic resin, and by being placed in a molten state, make it possible to join the thermoplastic tubes of the same diameter. Further, each of the bags 18 may be fixed to ends of the respective tubes 16 in a non-separable manner, and may have a structure for ensuring sterility inside the cell culturing kit 12. Alternatively, the cell culturing kit 12 may apply a connection structure (not shown) that enables a detachable connection between the tubes 16 and each of the bags 18.

Although not particularly limited, for the bioreactor 20 of the cell culturing kit 12, it may be beneficial to use a culturing base material having a large surface area, and in some embodiments, hollow fibers 24 that are applied thereto. More specifically, the bioreactor 20 includes a plurality of the hollow fibers 24 (e.g., ten thousand or more hollow fibers), and a cylindrical container 26 having a main space 26a (e.g., an internal space in the bioreactor 20) therein in which the plurality of hollow fibers 24 are accommodated.

The plurality of hollow fibers 24 extend along an axial direction of the container 26, and both ends thereof are retained by non-illustrated retaining walls of the container 26. Each of the hollow fibers 24 includes an internal cavity (not shown) that penetrates therethrough along the direction in which the hollow fiber 24 extends. The diameters of the hollow cavities, for example, are formed on the order of approximately 200 micrometers, and communicate with end spaces 26b on both sides in the axial direction that are partitioned by the retaining walls.

A membrane structure of the hollow fibers 24 that surrounds the internal cavities is formed by a porous body having a large number of pores. The pores communicate between an outer side (the main space 26a) of the hollow fibers 24 and the internal cavities, and are formed with sizes that regulate the passage of cells and proteins while enabling solutions and substances of low molecular weight to pass therethrough. The diameter of the pores is set, for example, on the order of 0.005 to 10 micrometers.

The material that makes up the membrane structure of the hollow fibers 24 is not particularly limited, but as examples include polyolefin resins such as polypropylene, polyethylene, and the like; and polymer materials such as polysulfone, polyether sulfone, polyacrylonitrile, polytetrafluoroethylene, polystyrene, polymethylmethacrylate, cellulose acetate, cellulose triacetate, regenerated cellulose, and/or the like.

The above-described hollow fibers 24 are capable of seeding (e.g., attaching, etc.) the cells to the inner circumferential surfaces of the internal cavities, and thereafter, supplying the culture medium and a predetermined gas component or the like to the cells through the internal cavities and the pores. Hereinafter, in the cell culturing system 22, a circulation flow path in which liquid is primarily circulated in the internal cavities of the hollow fibers 24 is referred to as an inner side circulation flow path or an intracapillary (IC) flow path. Further, a circulation flow path in which liquid is primarily circulated on an outer side of the hollow fibers 24 is referred to as an outer side circulation flow path or an extracapillary (EC) flow path.

The container 26 has an axial length which is capable of accommodating the hollow fibers 24 when the hollow fibers 24 are extended in a substantially linear shape. The container 26 is equipped with four terminals 28 (e.g., a first IC terminal 28a, a second IC terminal 28b, a first EC terminal 28c, and a second EC terminal 28d) that are connected respectively to the tubes 16. The first IC terminal 28a is provided at one end of the container 26 and communicates with the end space 26b on one end side. The second IC terminal 28b is provided at another end of the container 26 and communicates with the end space 26b on another end side. The first EC terminal 28c is provided on an outer peripheral surface of the container 26 in the vicinity of the other end side, and communicates with the main space 26a at a location in proximity to the other end. The second EC terminal 28d is provided on an outer peripheral surface of the container 26 in the vicinity of the one end side, and communicates with the main space 26a at a location in proximity to the one end.

The plurality of tubes 16 of the cell culturing kit 12 include a cell solution tube 16A connected between the cell solution bag 18A and the flow path cassette 10, a cleaning solution tube 16B connected between the cleaning solution bag 18B and the flow path cassette 10, a culture medium tube 16C connected between the culture medium bag 18C and the flow path cassette 10, a waste liquid tube 16D connected between the waste liquid bag 18D and the flow path cassette 10, a collection tube 16E connected between the collection bag 18E and the flow path cassette 10, a first IC tube 16F connected between the first IC terminal 28a of the bioreactor 20 and the flow path cassette 10, a second IC tube 16G connected between the second IC terminal 28b of the bioreactor 20 and the flow path cassette 10, a first EC tube 16H connected between the first EC terminal 28c of the bioreactor 20 and the flow path cassette 10, and a second EC tube 16I connected between the second EC terminal 28d of the bioreactor 20 and the flow path cassette 10.

A gas exchanger 29 that mixes a predetermined gas component with a liquid (e.g., the culture medium) is provided at an intermediate position of the first EC tube 16H. An example of the gas component to be mixed may be a gas component that approximates the mixing ratio of natural air (e.g., nitrogen $N_2$: 75%, oxygen $O_2$: 20%, and carbon dioxide $CO_2$: 5%).

The structure of the gas exchanger 29 is not particularly limited, and in the same manner as the bioreactor 20, a structure can be applied in which a plurality of hollow fibers 29b are provided inside a container 29a. More specifically, the gas exchanger 29 guides the liquid flowing through the first EC tube 16H, into the internal cavities of the hollow fibers 29b, and during movement thereof inside the hollow fibers 29b, the gas component that is supplied to the interior of the container 29a (the space on the outer side of the hollow fibers 29b) is mixed with the liquid through the pores of the hollow fibers 29b.

By joining the aforementioned tubes 16 in advance, the flow path cassette 10, which is one component of the cell culturing kit 12, functions as a liquid pathway relay unit through which the cell solution, the cleaning solution, the culture medium, and the release solution of the respective bags 18 are allowed to flow into a different bag 18 or the bioreactor 20. When the cell culturing kit 12 is set in the cell culturing device 14, the flow path cassette 10 is mounted in a non-illustrated cassette placement location inside the cell culturing device 14, which simplifies the wiring operation of the tubes 16 in the culturing process.

Figure 2:
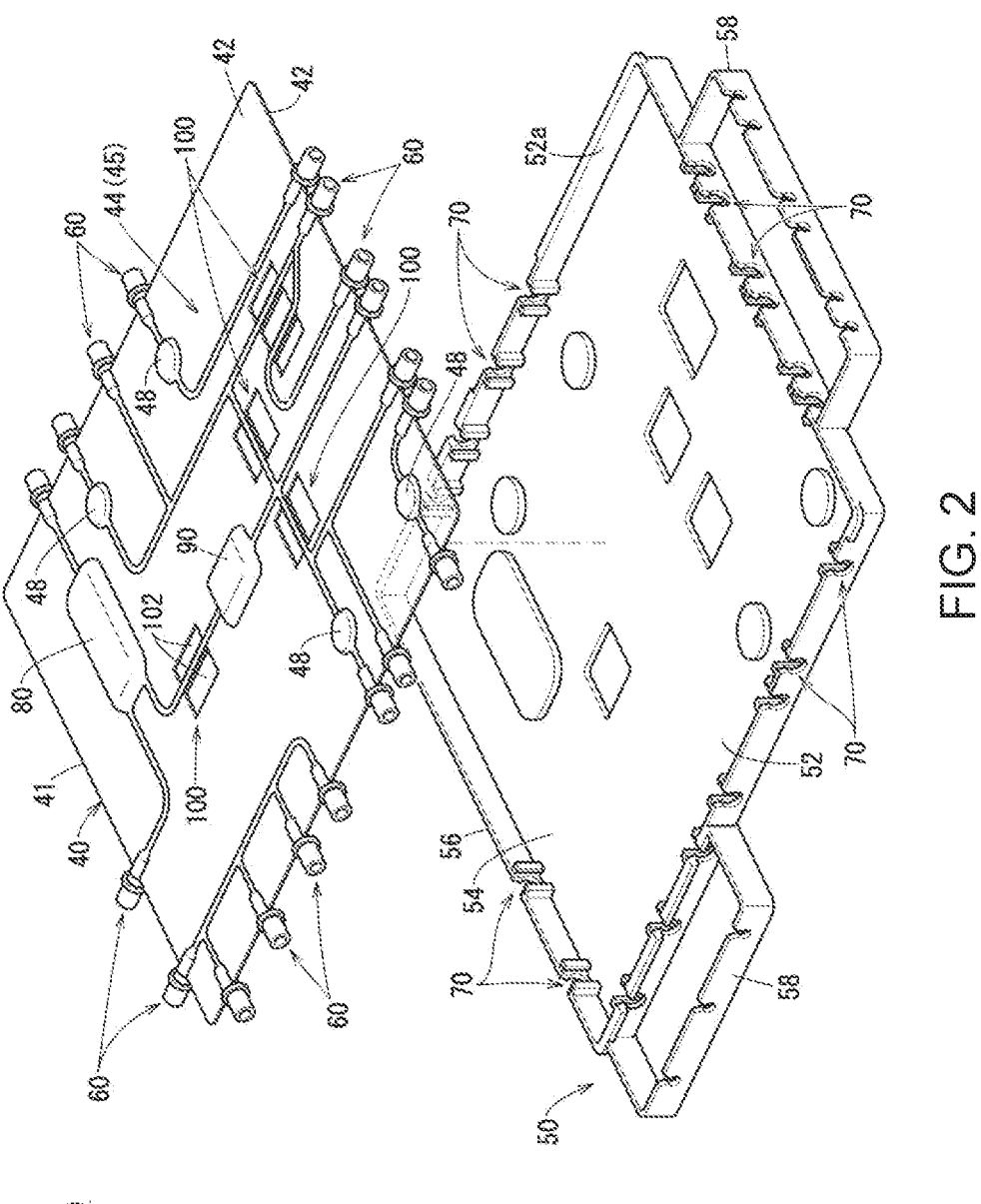
FIG. 2 is an exploded perspective view of a flow path cassette according to at least one embodiment of the present disclosure.

As shown in FIG. 2, the flow path cassette 10 includes a soft cassette main body 40 to which the plurality of tubes 16 are directly connected, and a rigid frame 50 that retains the cassette main body 40 and is fixed to the cell culturing device 14.

The cassette main body 40 exhibits a substantially rectangular shape, and is formed in a thin sheet shape which possesses flexibility. The cassette main body 40 is formed by stacking and joining (e.g., via fusion bonding) together two resin sheets 42 made of a resin material in a thickness direction. In the fusion bonding of the pair of resin sheets 42, gas is supplied to and discharged from between the pair of resin sheets 42 along grooves that are formed in a fusion bonding mold, whereby flow path walls, in which the resin sheets 42 are raised and protrude with semicircular shapes in cross-section, and flow paths 44 are formed on the inner sides thereof. The material of the resin sheets 42 is not particularly limited, insofar as it possesses flexibility that is capable of being deformed by the pressure of the liquids, and for example, a vinyl chloride resin, a polyolefin resin, a polyurethane resin, or the like may be applied thereto. An embossing process may be implemented on the surface of the cassette main body 40, and fine convex/concave irregularities may be formed therein. A plurality of connectors 60 for connection between the plurality of tubes 16 and the flow paths 44 are provided on outer edges 41 of the cassette main body 40.

On the other hand, the frame 50 is formed by a resin material that is harder (having a greater modulus of elasticity) than the cassette main body 40, and is formed in a thin recessed shape having an accommodation space 52 therein in which the cassette main body 40 is accommodated. The material of the frame 50 is not limited to any particular material; however, a thermoplastic resin material, for example, polypropylene, polycarbonate, polyamide, polysulfone, polyarylate, methacrylate-butylene-styrene copolymer, or the like may be used.

The frame 50 includes a substantially rectangular shaped cover portion 54 which is slightly larger than the cassette main body 40, and side portions 56 that protrude a short length from the outer periphery of the cover portion 54 in a direction perpendicular to the cover portion 54. The side portions 56 extend around the entire outer periphery of the cover portion 54. In the frame 50, the accommodation space 52 is opened through an opening 52a surrounded by the side portions 56 on an opposite side from the cover portion 54, thereby causing one surface of the cassette main body 40 to be exposed. Further, the frame 50 includes retaining frames 58 that extend outward from the upper side and the right side of the side portions 56, and retains the tubes 16 which are separated a predetermined distance from the side portions 56. Engaging portions 70 in which the respective connectors 60 are arranged and retained therein are provided in the side portions 56 at positions corresponding to the respective connectors 60 of the cassette main body 40.

The connectors 60 and the engaging portions 70 are disposed on four sides of the substantially rectangular shaped flow path cassette 10. By the connectors 60 and the engaging portions 70 on the four sides, the frame 50 retains the sheet-shaped cassette main body 40 in a stretched state, and suitably causes the flow paths 44 to be extended along a planar direction.

Figure 3:
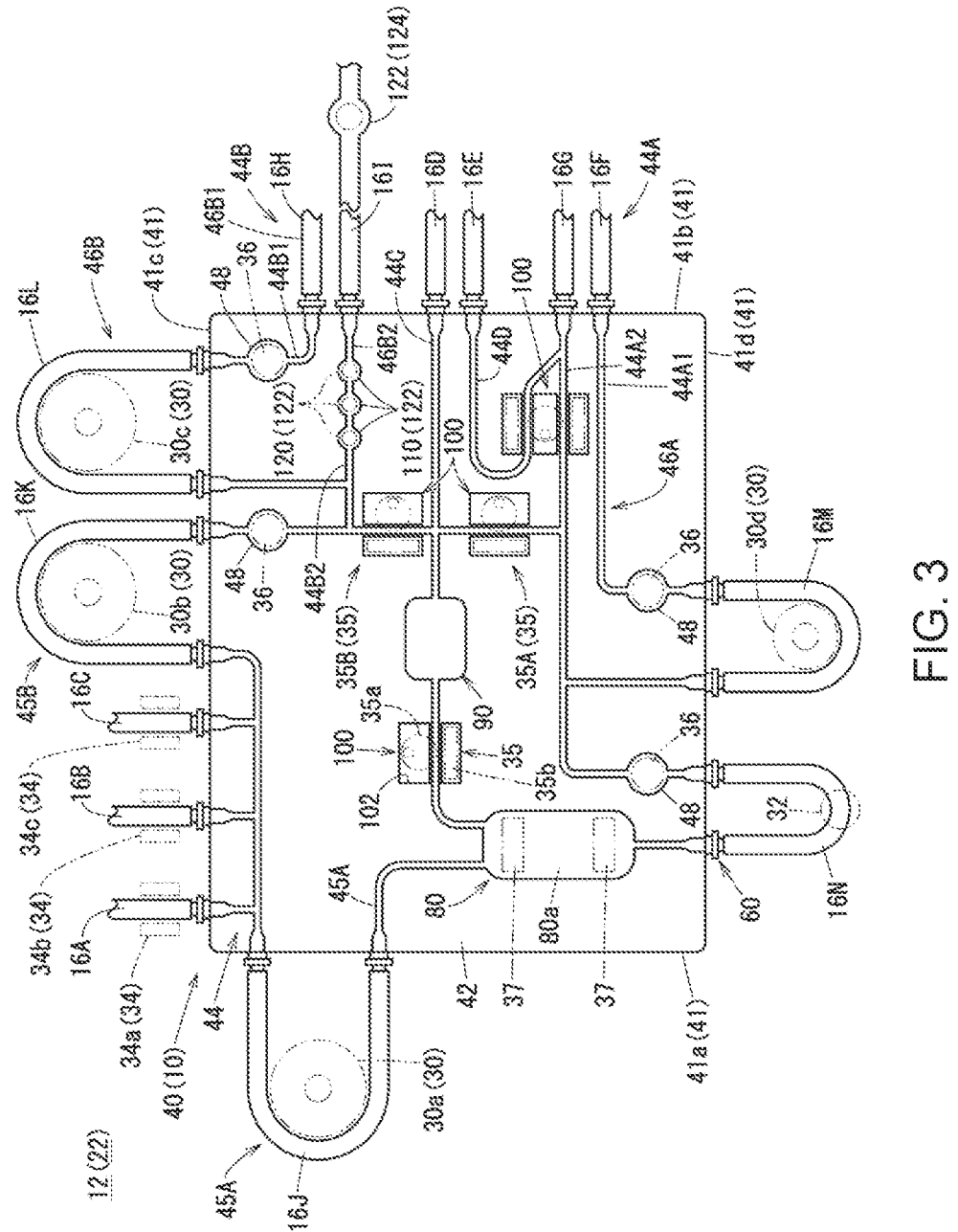
FIG. 3 is a plan view showing a cassette main body and a peripheral portion thereof according to at least one embodiment of the present disclosure.

As shown in FIG. 3, the flow path cassette 10 is set inside the cell culturing device 14 such that the cassette main body 40 and the frame 50 are integrated, and the planar direction of the cassette main body 40 is set in an upright posture along the direction of gravity (e.g., in the vertical direction). Moreover, the flow path cassette 10 in FIG. 3 is shown in a posture as viewed from the cover portion 54 (the side of a touch panel 134 of the cell culturing device 14) in a state of being mounted in the cell culturing device 14, and in order to simplify description, the frame 50 is omitted and only the cassette main body 40 is shown.

More specifically, the outer edges 41 of the cassette main body 40 may include a first short side 41a (e.g., as shown in the left-hand side of FIG. 3), a second short side 41b (as shown in the right-hand side of FIG. 3), a first long side 41c (as shown in the upper side of FIG. 3), and a second long side 41d (as shown in the lower side of FIG. 3). The cell solution tube 16A, the cleaning solution tube 16B, and the culture medium tube 16C are connected to the first long side 41c. The waste liquid tube 16D, the collection tube 16E, the first IC tube 16F, the second IC tube 16G, the first EC tube 16H, and the second EC tube 16I are connected to the second short side 41b.

Further, in the cell culturing system 22, in the set state, four pumps 30 are arranged at positions in proximity to the sides of the flow path cassette 10. More specifically, in the set state, the cell culturing device 14 includes a first pump 30a disposed in proximity to the first short side 41a, a second pump 30b and a third pump 30c disposed in proximity to the first long side 41c, and a fourth pump 30d disposed in proximity to the second long side 41d. The first to fourth pump tubes 16J to 16M, which project out from the flow path cassette 10, are wound around the first to fourth pumps 30a to 30d, and by being rotated in a squeezing manner around the pump tubes 16J to 16M, the first to fourth pumps 30a to 30d cause the liquids inside the pump tubes 16J to 16M to flow.

The first pump 30a serves to guide the liquid to flow in an IC route 44A to be described later, and the second pump 30b serves to guide the liquid to flow in an EC route 44B to be described later. On the other hand, the third pump 30c circulates the liquid of the EC route 44B, and the fourth pump 30d circulates the liquid of the IC route 44A.

Further, in the cell culturing system 22, in the set state, the air bubble sensor 32 is arranged with respect to the sensor tube 16N of the cassette main body 40. Furthermore, in the set state, outer side clamps 34 that open and close internal flow paths are arranged on the cell solution tube 16A, the cleaning solution tube 16B, and the culture medium tube 16C. More specifically, a first outer side clamp 34a is arranged on the cell solution tube 16A, a second outer side clamp 34b is arranged on the cleaning solution tube 16B, and a third outer side clamp 34c is arranged on the culture medium tube 16C.

Further, as noted previously, the flow paths 44 having predetermined shapes are formed inside the cassette main body 40, and extend along the planar direction. Furthermore, inside the cassette main body 40, a plurality of pressure target detection units 48, a liquid level target detection unit 80, a check valve unit 90, which are in communication with the flow paths 44, and a plurality of flow path opening/closing units (e.g., flow path opening and closing units) 100 and a plurality of parameter target detection units 110, which are configured together with the flow paths 44, are provided.

In some examples, the plurality of flow path opening/closing units 100 may correspond to one or more pinch valves. Moreover, part of the parameter target detection units 110 are disposed at intermediate positions of the tubes 16 (the second IC tube 16G and the second EC tube 16I, etc.) on an external part of the flow path cassette 10.

Although detailed description thereof is omitted, the flow paths 44 may be made up from the IC route 44A for supplying liquid to the internal cavities of the hollow fibers 24 together with the first and second IC tubes 16F and 16G, and the EC route 44B for supplying liquid to the outer side (the main space 26a) of the hollow fibers 24 together with the first and second EC tubes 16H and 16I. In particular, in a culturing step of supplying the culture medium to the bioreactor 20, the outer side clamps 34 and the inner side clamps 35 of the cell culturing device 14 are appropriately opened or closed, whereby the IC route 44A and the EC route 44B are placed in the state shown schematically in FIG. 4.

Figure 4:
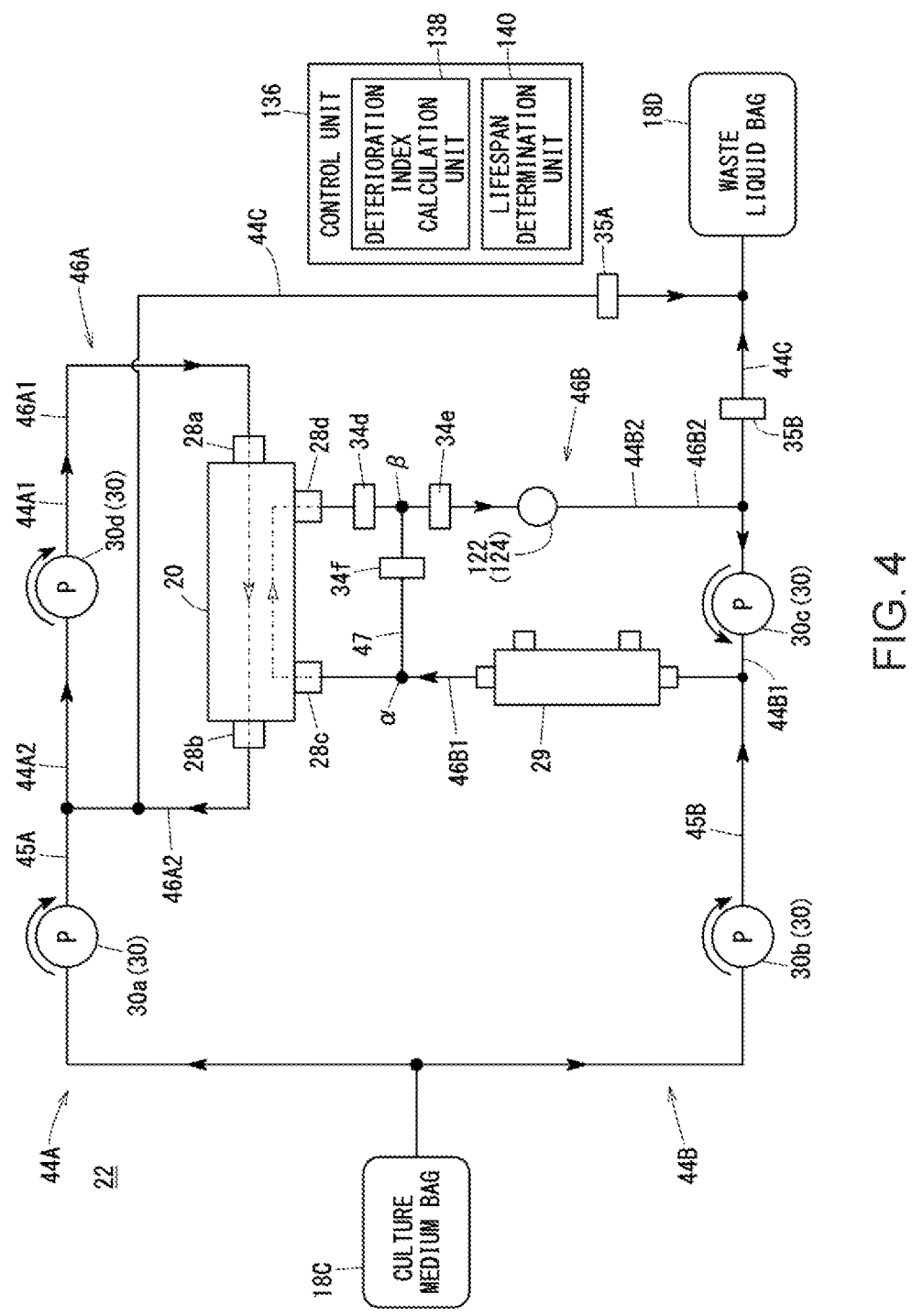
FIG. 4 is a schematic diagram showing liquid pathways of the cell culturing system at a time of cell culturing according to at least one embodiment of the present disclosure.

As shown in FIGS. 3 and 4, the IC route 44A includes inside the cassette main body 40 a first IC port path 44A1 (as shown in FIG. 3) in communication with the first IC tube 16F, and a second IC port path 44A2 (as shown in FIG. 3) in communication with the second IC tube 16G. The IC route 44A includes an IC supply circuit 45A that delivers out the respective liquids of the cell solution bag 18A, the cleaning solution bag 18B, and the culture medium bag 18C, and supplies the liquids to a downstream side. Further, the IC route 44A includes an IC circulation circuit 46A provided on a downstream side of the IC supply circuit 45A, and which circulates the liquids between the bioreactor 20 and the IC route 44A. The IC circulation circuit 46A forms an IC inflow pathway 46A1 through which the liquid is allowed to flow into the internal cavities of the hollow fibers 24 by the first IC tube 16F and the first IC port path 44A1, and also forms an IC outflow pathway 46A2 through which the liquid is allowed to flow out from the internal cavities of the hollow fibers 24 by the second IC tube 16G and the second IC port path 44A2.

The EC route 44B includes, in the interior of the cassette main body 40, a first EC port path 44B1 in communication with the first EC tube 16H, and a second EC port path 44B2 in communication with the second EC tube 16I. The EC route 44B includes an EC supply circuit 45B that delivers out the respective liquids of the cell solution bag 18A, the cleaning solution bag 18B, and the culture medium bag 18C, and supplies the liquids to a downstream side. Further, the EC route 44B includes an EC circulation circuit 46B that circulates the liquid between the bioreactor 20 and the EC route 44B on a downstream side of the EC supply circuit 45B. The EC circulation circuit 46B forms an EC inflow pathway 46B1 through which the liquid is allowed to flow into the main space 26a by the first EC tube 16H and the first EC port path 44B1, and also forms an EC outflow pathway 46B2 through which the liquid is allowed to flow out from the main space 26a by the second EC tube 16I and the second EC port path 44B2.

The pressure target detection units 48 of the cassette main body 40 are provided on downstream sides of the pumps 30 in the IC route 44A and the EC route 44B. The pressure target detection units 48, in the set state, are arranged so as to face the pressure sensors 36 of the cell culturing device 14, and serve to detect the pressures in the flow paths 44. Further, the liquid level target detection unit 80 is provided in the IC route 44A, temporarily stores the flowing liquid in a storage space 80a, and causes the liquid to flow out to the IC route 44A, together with causing gas to flow out to a route that differs from that for the liquid. The liquid level target detection unit 80 is arranged so as to face the liquid level sensors 37 of the cell culturing device 14, and serves to detect the liquid level of the liquid stored in the interior thereof. The check valve unit 90 is provided in a route from which the gas is allowed to flow out from the liquid level target detection unit 80, and restricts inflowing of gas or liquid into the liquid level target detection unit 80 from such a route.

The flow path opening/closing units 100 may include a plurality of cutaways 102, and are disposed in the respective plurality of inner side clamps 35 of the cell culturing device 14. The inner side clamps 35 include displacement bodies 35a and fixed bodies 35b that are inserted into the cutaways 102, and that, by bringing the displacement bodies 35a in proximity to the fixed bodies 35b, close the predetermined flow paths 44, and by moving the displacement bodies 35a away from the fixed bodies 35b, open the predetermined flow paths 44. The flow path opening/closing units 100 are provided on the aforementioned gas outflow route, a waste liquid route 44C from the IC route 44A or the EC route 44B to the waste liquid bag 18D, a collection route 44D from the IC route 44A to the collection bag 18E, and the second IC port path 44A2. Hereinafter, the inner side clamp 35 from the IC route 44A toward the waste liquid bag 18D is referred to as an IC waste liquid clamp 35A, and the inner side clamp 35 from the EC route 44B toward the waste liquid bag 18D is referred to as an EC waste liquid clamp 35B.

The parameter target detection units 110 are capable of detecting parameters related to culturing of cells in the liquid that flows in the bioreactor 20. The parameters related to culturing of cells may include, but are in no way limited to, an amount of dissolved oxygen, a pH, an amount of glucose, an amount of dissolved carbon dioxide, and an amount of lactic acid of the culture medium (e.g., liquid) that flows in the flow paths 44. The amount of dissolved oxygen, the pH, and the amount of glucose correspond to parameters of the culturing environment of the cells. The pH, the amount of dissolved carbon dioxide, and the amount of lactic acid correspond to parameters related to metabolism of the cells (e.g., the bioactivity of the cells). Moreover, since the pH also is changed depending on the concentration of the metabolite, the pH changes depend on the metabolite and the metabolism of the cells. One of the parameter target detection units 110 is capable of detecting any one of these five types of parameters.

More specifically, the culture parameter detection units 122 include the parameter target detection units 110, the cell culturing device 14, and enzyme sensors 124, and serve to detect parameters related to the cells when culturing of the cells is carried out. The cell culturing device 14 records and adjusts (e.g., with a feedback loop) the amounts of the culture medium and the gas component supplied to the bioreactor 20, on the basis of the detection results of the culture parameter detection units 122.

In some embodiments, a plurality of parameter target detection units 110 (e.g., three units) of the flow path cassette 10 shown in FIG. 3 are provided in the second EC port path 44B2, and detect different types of parameters, respectively, from among an amount of dissolved oxygen, a pH, an amount of glucose, an amount of dissolved carbon dioxide, and an amount of lactic acid. Moreover, only one parameter target detection unit 110 may be provided for detecting one type of parameter, or five of such units may be provided in order to detect all five types of parameters. The parameters detected by the parameter target detection units 110 (and/or the culture parameter detection units 122) are not limited to the five types described above, and it is a matter of course that they may be applied to every type of component necessary for culturing. For example, other parameters may include, the number of cells, glutamine, ammonium ion, proteins, and the like. The parameter target detection units 110 (and/or the culture parameter detection units 122) may be provided in an appropriate number according to the types of components to be detected. Furthermore, the parameter target detection units 110 are not limited to being disposed in the second EC port path 44B2, and may be disposed in another one of the flow paths 44 (e.g., the second IC port path 44A2).

The parameter target detection units 110 include fluorescent chips (not shown) in the interior of bulging portions that communicate with the flow paths 44 and whose flow path cross-sectional area is widened. The parameter target detection units 110, in the set state, are arranged respectively at positions facing toward the sensors 120 of the cell culturing device 14. The fluorescent chips include a laminated structure that enables optical measurement of predetermined parameters related to culturing of cells. One layer of the laminated structure is a target detection layer that undergoes coloring in response to a predetermined substance contained in the culture medium.

For each of the sensors 120 of the cell culturing device 14, there may be an optical sensor having a light emitting unit that emits measurement light, and a light receiving unit that receives excitation light generated from the fluorescent chips (neither of which is shown). Each of the sensors 120, under the control of the cell culturing device 14, emits toward each of the fluorescent chips measurement light having a wavelength corresponding to the characteristics of the fluorescent chips, and receives excitation light generated from the fluorescent chips. Consequently, the sensors 120 transmit to a control unit 136 detection signals based on the degree of coloration of the fluorescent chips.

Figure 5B:
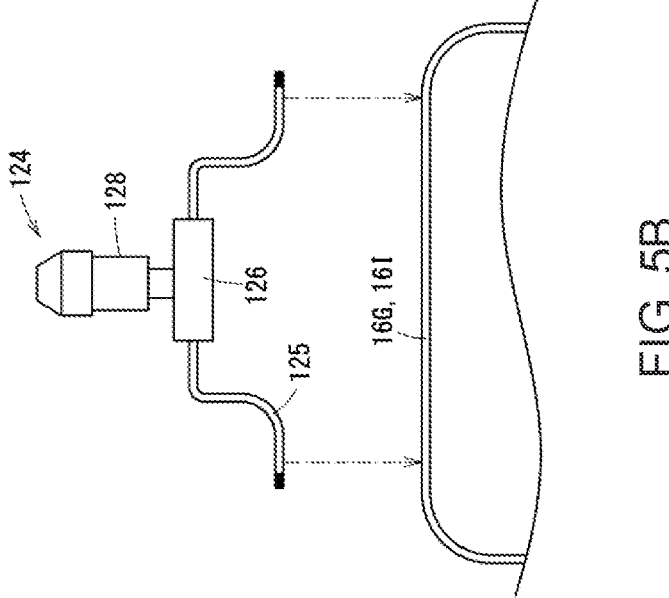
FIG. 5B is an schematic plan view showing a method of attaching the enzyme sensor according to at least one embodiment of the present disclosure.
Figure 5A:
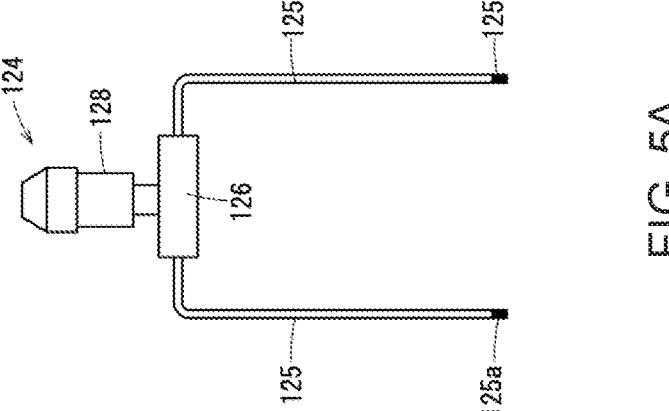
FIG. 5A is a plan view showing an example of an enzyme sensor according to at least one embodiment of the present disclosure.

Further, according to the present embodiment, as the culture parameter detection units 122 of the flow path cassette 10, as shown in FIG. 5B, enzyme sensors 124 that detect the amount of glucose and the amount of lactic acid are installed in intermediate locations of the second IC tube 16G, the second EC tube 16I, and the like. As shown in FIG. 5A, each of the enzyme sensors 124 has a structure in which a sensor main body 128 and a pair of tubes 125 are connected to a T-shaped joint 126. In the interior of the joint 126, a detection unit of the sensor main body 128 is exposed. Each of the detection units includes an electrode and an enzyme fixation layer, and a substance change, which is generated by a reaction of the enzyme with a substance to be measured (e.g., lactic acid or glucose) within the culture medium flowing inside the joint 126, is electrochemically detected as a current value by the electrode. The tubes 125 connected to the joint 126 are retained in a state of being sealed by fusion bonded portions 125a.

As shown in FIG. 5B, when placed in use, the enzyme sensors 124 are joined to the tubes 16 (e.g., the second IC tube 16G, the second EC tube 16I, etc.) that serve as installation targets, using a commercially available aseptic joining device. Further, replacement of the enzyme sensors 124 may be performed by connecting a new enzyme sensor 124 to the tubes 16 serving as the installation targets in place of the deteriorated enzyme sensor 124, using a commercially available aseptic joining device.

The cell culturing system 22 described above executes a step of culturing cells by circulating the culture medium with respect to the bioreactor 20 for a long time period (e.g., several days), and at this time, the state (as, for example, determined by measuring the parameters) of the culture medium continues to be detected by the culture parameter detection units 122. Further, the cell culturing system 22 determines the lifespan of the culture parameter detection units 122 (based on, for example, the enzyme sensors 124) at an appropriate timing during culturing, in order to stabilize the detection accuracy of the culture parameter detection units 122 during culturing. The method of determining the lifespan of the enzyme sensors 124 will be described later.

The cell culturing kit 12 includes a bypass pathway 47 in the EC route 44B in which the culture parameter detection units 122 are disposed. The bypass pathway 47 is configured by a bypass tube 16O connected between the first EC tube 16H and the second EC tube 16I. One end of the bypass tube 16O is connected to a connection point alpha (α) of the first EC tube 16H between the gas exchanger 29 and the bioreactor 20 (the first EC terminal 28c). On the other hand, the other end of the bypass tube 16O is connected to a connection point beta (β) of the second EC tube 16I connected between the bioreactor 20 and the parameter target detection units 110. For example, the first or second EC tubes 16H and 16I and the bypass tube 16O are connected via a 3-port connector 142 or the like.

Further, in the cell culturing system 22, in a state in which the cell culturing kit 12 is set in the cell culturing device 14, a plurality of the outer side clamps 34 are arranged in the vicinity of the connection point beta between the EC outflow pathway 46B2 and the bypass pathway 47. More specifically, the cell culturing device 14 includes a main clamp 34d arranged on the second EC tube 16I on an upstream (bioreactor 20) side of the connection point beta, and an auxiliary clamp 34e arranged on a downstream side (e.g., proximate the culture parameter detection units 122) of the connection point beta. Further, the cell culturing device 14 includes a sub-clamp 34f arranged on the bypass tube 16O.

During culturing of the cells, the main clamp 34d, the auxiliary clamp 34e, and the sub-clamp 34f open and close the respective internal flow paths of the respective tubes under the operation of the cell culturing device 14. For example, the cell culturing system 22 opens the main clamp 34d and the auxiliary clamp 34e, while on the other hand, closes the sub-clamp 34f, in the case that the culture medium is supplied to the bioreactor 20 during culturing of the cells. Consequently, the culture medium in the first EC tube 16H is smoothly introduced into the bioreactor 20. On the other hand, in the case that replacement of the enzyme sensor 124 is performed, the cell culturing system 22 closes the auxiliary clamp 34e and stops the third pump 30c.

It should be noted that the configuration for changing the flow pathways of the culture medium is not limited to the above-described main clamp 34d, the auxiliary clamp 34e, and the sub-clamp 34f. For example, the main clamp 34d may be disposed on the EC inflow pathway 46B1 between the connection point alpha and the bioreactor 20. Further, for example, the cell culturing system 22 may be configured so as not to be equipped with the auxiliary clamp 34e.

Returning to FIG. 1, the cell culturing device 14 in which the cell culturing kit 12 is mounted is equipped with a box-shaped device main body 130, and a stand 132 on which the bags 18 of the cell culturing kit 12 are retained. Further, a touch panel 134 (e.g., a display operation unit) for carrying out operations and displays when the culturing process is performed is provided on an outer surface of the device main body 130. Furthermore, in the interior of the device main body 130, there are provided a cassette placement location (not shown) in which the flow path cassette 10 is fixed in an upright posture, and the bioreactor 20 is retained at an appropriate height, and the control unit 136 that controls operations of the cell culturing system 22.

The control unit 136 includes a processor, a memory, and an input/output interface (not shown), and by the processor executing a program stored in the memory, in the culturing process, the pumps 30, the outer side clamps 34, the inner side clamps 35, etc., are appropriately operated. In particular, during culturing of the cells (e.g., when supplying the culture medium), the control unit 136 receives detection signals from each of the sensors 120, and adjusts (e.g., feedback controls) driving of the pumps 30 on the basis of the detection results thereof. Further, as shown in FIG. 4, the control unit 136 is equipped with a deterioration index calculation unit 138 that calculates (e.g., integrates), based on the detected concentration value of the enzyme sensors 124, a deterioration index, which is reflective of how long the enzyme sensors 124 have been in contact with how much of a concentration of the culture medium, and a lifespan determination unit 140 that determines a lifespan of the enzyme sensors 124 by comparing an integrated value of the deterioration index and a predetermined threshold value. The lifespan determination unit 140 determines the lifespan of the culture parameter detection units 122 (e.g., the enzyme sensors 124) at an appropriate timing during culturing of the cells. It should be noted that sensors other than an enzyme sensor 124 (such as a temperature sensor, a glucose sensor, etc.), while not illustrated, may be present.

For example, when the control unit 136 receives a detection result of the enzyme sensor 124 that detects the amount of lactic acid, the control unit 136 calculates the amount of lactic acid using an appropriate calculation formula or information of a calibration curve that is stored in advance. In addition, the deterioration index calculation unit 138 of the control unit 136 calculates a concentration time value, which is obtained by multiplying an elapsed time (e.g., a detection period) from a previous measurement timing and the detected concentration value, and updates the deterioration index by adding the concentration time value to the deterioration index, which is an integrated value of the concentration time values in the past. Further, the lifespan determination unit 140 of the control unit 136 compares a threshold value of the deterioration index, at which the detection sensitivity of the enzyme sensor 124 starts to decrease (the threshold value being experimentally obtained in advance) with the deterioration index that was calculated by the deterioration index calculation unit 138, and thereby determines the lifespan of the enzyme sensor 124.

Furthermore, the control unit 136 calculates a number of cells on the basis of the calculated amount of lactic acid and the stored calibration information, and based on the calculated number of cells, adjusts the supplied amount (where supply rate may be determined based on the rotational speed of the pumps 30) of the culture medium that should be supplied to the bioreactor 20.

The cell culturing kit 12 and the cell culturing system 22 according to the present embodiment are configured similar to or in the same manner as described above. Next, a description will be given below concerning operations thereof.

As shown in FIG. 1, in an expansion process of the cell culturing system 22, an operator inserts portions of the cell culturing kit 12 including the flow path cassette 10 into the cell culturing device 14. Further, the operator places the appropriate tubes 16 of the cell culturing kit 12 on the pumps 30, the air bubble sensor 32, and the outer side clamps 34 of the cell culturing device 14. Furthermore, when the flow path cassette 10 is arranged, the inner side clamps 35 are disposed on the flow path opening/closing units 100, and the sensors 120 are disposed on the parameter target detection units 110. Consequently, as shown in FIG. 3, the flow path cassette 10 is set in the cell culturing device 14 in such a posture that the planar direction thereof is oriented along the direction of gravity. Furthermore, the bags 18 of the cell culturing kit 12 are also suspended from the stand 132 by the operator.

Figures 6A, 6B:
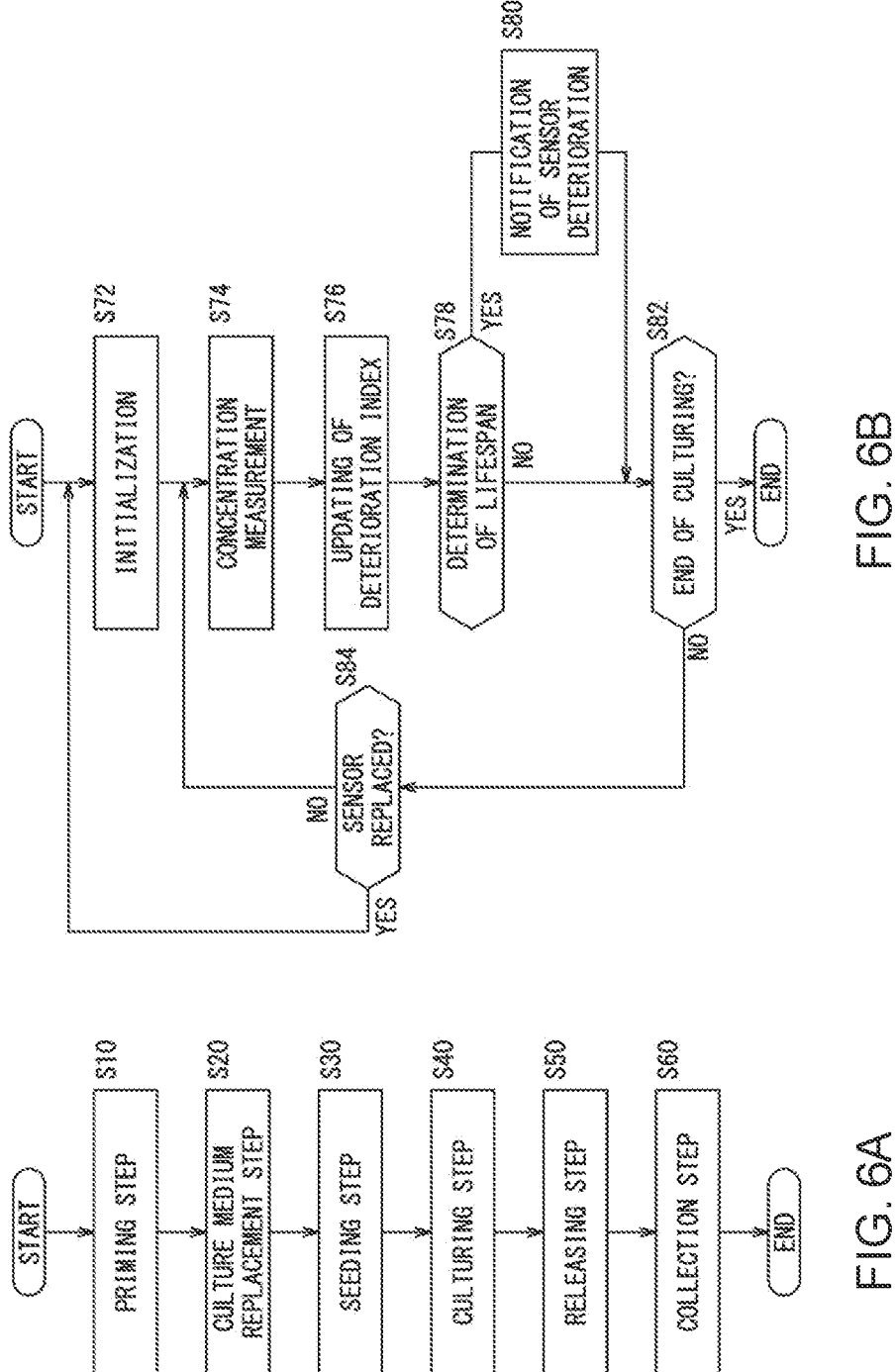
FIG. 6A is a flowchart showing a method of treatment of the cell culturing system according to at least one embodiment of the present disclosure.
FIG. 6B is a flowchart showing a method of determining a lifespan of the enzyme sensor in a culturing step according to at least one embodiment of the present disclosure.

After having been set, in the expansion process, as shown in FIG. 6A, a priming step (S10), a culture medium replacement step (S20), a seeding step (S30), a culturing step (S40), a releasing step (S50), and a collection step (S60) are sequentially performed.

In the priming step (S10), the cleaning solution in the cleaning solution bag 18B is made to flow through the two routes (e.g., through the IC route 44A and the EC route 44B) inside the flow path cassette 10, and the gas existing in the predetermined tubes 16, the bioreactor 20, and the routes of the cassette main body 40 is removed. Further, the removed gas is guided to the waste liquid bag 18D.

In the culture medium replacement step (S20), in the same manner as in the priming step (S10), the culture medium in the culture medium bag 18C is guided into the predetermined tubes 16, the bioreactor 20, and the routes of the cassette main body 40, which are then filled with the culture medium. In the seeding step (S30) after having performed the culture medium replacement step (S20), the cell solution of the cell solution bag 18A is supplied via the IC route 44A to the internal cavities of the hollow fibers 24 of the bioreactor 20, and at the same time, the culture medium existing in the EC route 44B is circulated, and the gas component is supplied to the bioreactor 20.

In addition, in the culturing step (S40) after having performed the seeding step (S30), as shown in FIG. 4, the culture medium is supplied from both the IC route 44A and the EC route 44B, and culturing of the cells that were seeded in the bioreactor 20 is carried out. Moreover, in the cell culturing system 22, an operation of supplying the culture medium from the EC route 44B without using the IC route 44A may be carried out in the culturing step (S40).

The culturing step (S40) is carried out for a longer period in comparison with the other steps, whereby the cells on the inner peripheral surfaces of the hollow fibers 24 are made to propagate (expand, or proliferate). Then, in the culturing step (S40), based on the process flow shown in FIG. 6B, the cell culturing system 22 determines the lifespan of the enzyme sensors 124.

Figure 7:
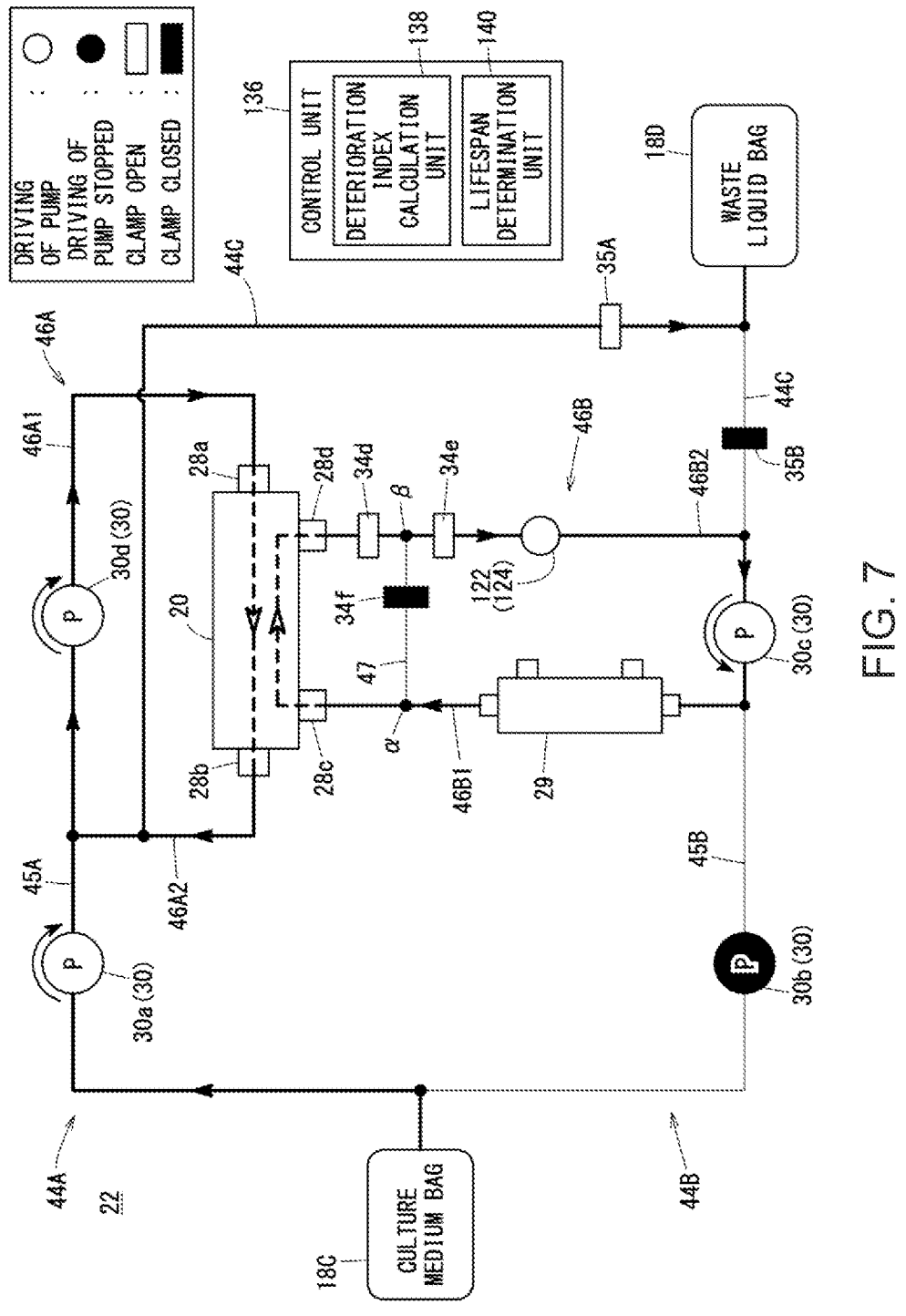
FIG. 7 is a schematic diagram showing operations of a normal time circulating step according to the at least one embodiment of the present disclosure.

As shown in FIG. 7, in the culturing step (S40), a normal time circulating step of supplying the culture medium to the bioreactor 20 and causing the cells to propagate inside the hollow fibers 24 is executed. In the normal time circulating step, the control unit 136 opens the main clamp 34d and the auxiliary clamp 34e, while on the other hand, closes the sub-clamp 34f. Stated otherwise, in the EC circulation circuit 46B, the EC inflow pathway 46B1 and the EC outflow pathway 46B2 are placed in a flow through state, whereas the bypass pathway 47 is placed in a state in which flow therethrough is blocked. Further, the control unit 136 opens the IC waste liquid clamp 35A, while on the other hand, closes the EC waste liquid clamp 35B. Consequently, the culture medium flows out from the IC route 44A into the waste liquid bag 18D, and the culture medium is circulated in the EC route 44B.

In accordance therewith, in the IC route 44A, under a driving action of the fourth pump 30d, the culture medium is circulated with respect to the bioreactor 20 (the internal cavities of the hollow fibers 24). Further, in the EC route 44B, under a driving action of the third pump 30c, the culture medium is supplied from the EC inflow pathway 46B1 into the main space 26a of the bioreactor 20 (e.g., the container 26). The culture medium in the IC route 44A and the EC route 44B is provided to the cells in the hollow fibers 24, and further, a portion of the culture medium flows out from the bioreactor 20 into the EC outflow pathway 46B2 via the main space 26a. The culture medium that has flowed out, in the course of flowing through the EC outflow pathway 46B2, passes through the parameter target detection units 110 (e.g., the culture parameter detection units 122) provided in the cassette main body 40. Therefore, the control unit 136 detects the state of the culture medium (e.g., the parameters of the amount of dissolved oxygen, the pH, and the amount of dissolved carbon dioxide, etc.), by the plurality of sensors 120, and based on the detection results, controls the supplied amount (e.g., a supply rate) of the culture medium.

Further, during execution of the normal time circulating step, the control unit 136 performs a lifespan determination process of the enzyme sensors 124, in accordance with steps S72 to S84 shown in FIG. 6B. In the lifespan determination process, first, in an initialization step (S72), the control unit 136 initially performs a process of returning the deterioration index of the deterioration index calculation unit 138 to an initial value of "0". Next, the control unit 136 carries out a concentration measurement step (S74) for measuring the concentration of a predetermined component (e.g., glucose or lactic acid) of the culture medium using the enzyme sensors 124.

Thereafter, the deterioration index calculation unit 138 of the control unit 136 performs a deterioration index updating step (S76). In the deterioration index updating step (S76), the deterioration index calculation unit 138 calculates a concentration time value by multiplying an elapsed time period (e.g., a detection period) from a previous concentration measurement step (S74) to the current concentration measurement step (S74), and the detected concentration value of the current concentration measurement step (S74). Then, the deterioration index calculation unit 138 updates the deterioration index by adding the concentration time value to past deterioration indexes (e.g., an integrated value of the concentration time values).

Next, the lifespan determination unit 140 of the control unit 136 performs a lifespan determination step (S78) of determining the lifespan of the enzyme sensors 124, based on whether or not the updated deterioration index exceeds the predetermined threshold value. In the lifespan determination step (S78), in the case that the lifespan determination unit 140 detects that the deterioration index is in excess of the threshold value (YES), a sensor deterioration notification step (S80) is performed, in which the control unit 136 carries out a display on the touch panel 134 to prompt replacement of the enzyme sensor 124. Thereafter, the process transitions to an end determination step (S82).

Further, in the lifespan determination step (S78), in case it is not detected by the lifespan determination unit 140 that the deterioration index is in excess of the threshold value (NO), the process transitions directly to the end determination step (S82). In the end determination step (S82), in the case that the control unit 136 terminates the culturing step (S40) (YES), the lifespan determination process is brought to an end.

On the other hand, in the end determination step (S82), in the case that the control unit 136 determines that the culturing step (S40) is not completed (NO), the process transitions to a sensor replacement detection step (S84). In the sensor replacement detection step (S84), the control unit 136 determines whether or not an enzyme sensor 124 has been replaced. In the case that the control unit 136 determines that the sensor has not been replaced (NO), the process transitions to the concentration measurement step (S74), and after the elapse of a predetermined period, the concentration of the culturing medium is measured again using the enzyme sensor 124. Further, in the case that the control unit 136 determines in the sensor replacement detection step (S84) that the enzyme sensor 124 has been replaced (YES), the process transitions to the initialization step (S72), and initialization of the integrated value of the deterioration index is performed.

Figure 8A:
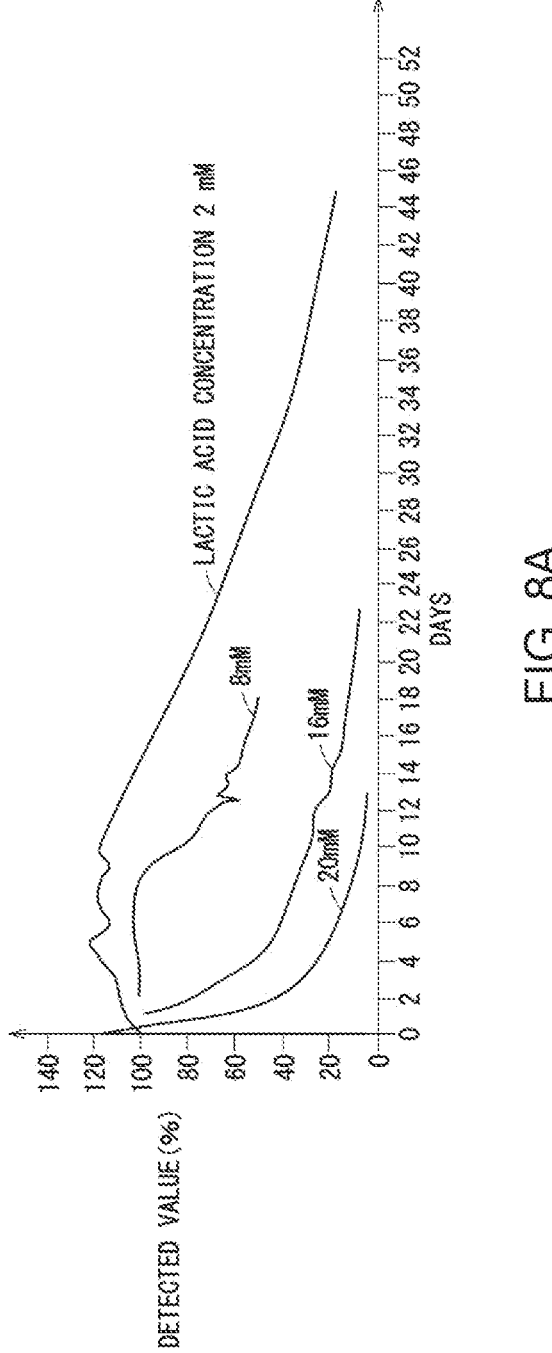
FIG. 8A is a graph showing a relationship between a substrate concentration of a culture medium and transitioning of a decrease in sensitivity of the enzyme sensor according to at least one embodiment of the present disclosure.
Figure 8B:
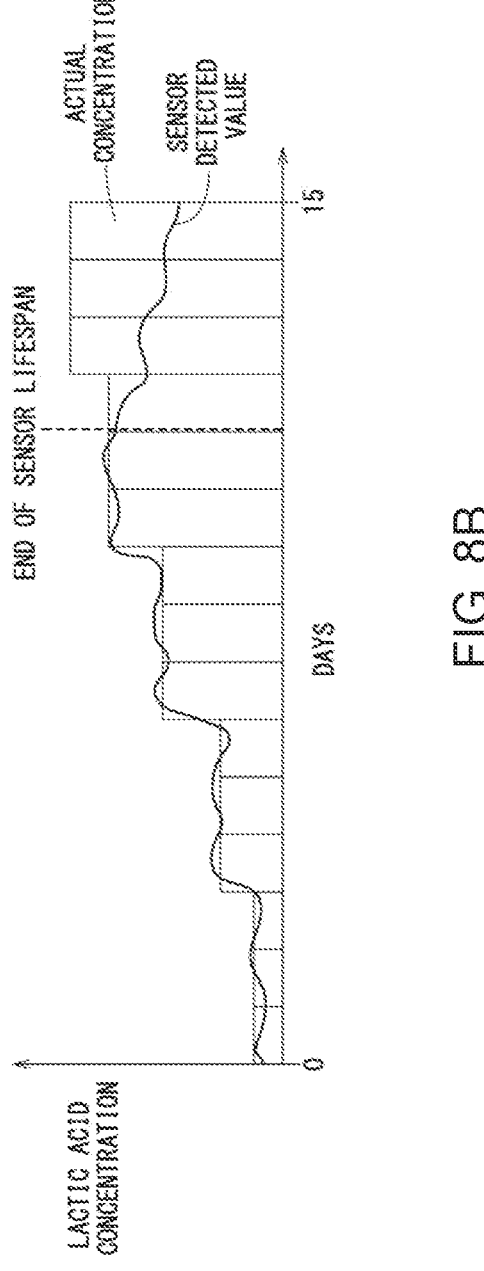
FIG. 8B is a graph showing a relationship between a change in the substrate concentration of the culture medium of the cell culturing system and a detected value of the enzyme sensor according to at least one embodiment of the present disclosure.

By carrying out the process described above, the lifespan of the enzyme sensors 124 is detected. As shown in FIG. 8B, in the cell culturing system 22, the lactic acid concentration in the culture medium gradually increases accompanying expansion of the cells. The detected value of the enzyme sensor 124 that measures the lactic acid concentration tracks with the change in the concentration of the lactic acid in the culture medium. However, as the lactic acid concentration increases, the deterioration gradually progresses more rapidly, and when the deterioration index exceeds the threshold value, the detection sensitivity of the enzyme sensor 124 is lowered, and a detected value which is lower than the actual concentration is output. The cell culturing system 22 detects the lifespan of the enzyme sensors 124, and carries out a display on the touch panel 134 to prompt replacement thereof, and thereby makes it possible to appropriately manage the culturing step (S40).

In this instance, concerning the manner of determining the threshold value in the lifespan determination step (S78), an example description will be given with reference to FIG. 8A of the measurement of the lactic acid concentration. The threshold value is determined experimentally in advance using an enzyme sensor 124 that is placed in use. As shown in FIG. 8A, test solutions are prepared having lactic acid concentrations of 2, 8, 16, and 20 millimoles (mM) or 0.001 moles per liter (mol/L). In addition, while each of the test solutions flows through the enzyme sensor 124, the detected value of the enzyme sensor 124 is measured at each of regular time intervals. As shown in the figure, the detection sensitivity of the enzyme sensor 124 exhibits a tendency of starting to decrease after a predetermined time period; however, the point in time at which the detection sensitivity starts to decrease tends to occur earlier as the lactic acid concentration increases. According to the present embodiment, based on the above-described experimental results, the threshold value is determined based on the lactic acid concentration, and a time period until the lactic acid concentration falls below an acceptable detection sensitivity (e.g., 80% of the initial value). For example, at a lactic acid concentration of 2 mM, in the case that the lactic acid concentration becomes less than the acceptable detection sensitivity on the 18th day from the start of measurement, the threshold value is calculated by 2 mM times 18 times 24 hours (hr) to thereby obtain 864 mM hr.

Next, in the culturing step (S40), a description will be given concerning operations of the cell culturing system 22 when the enzyme sensor 124 is replaced. In this case, the user issues an instruction to carry out an operation to replace the sensor through the touch panel 134. Consequently, the cell culturing system 22 closes the auxiliary clamp 34e of FIG. 7, and stops the culture medium from flowing to the enzyme sensor 124. Owing to this feature, by the method that was described with reference to FIG. 5B, the user can perform an operation of reconnecting a new enzyme sensor

124 using an aseptic joining device. After having replaced the enzyme sensor 124, the user issues an instruction through the touch panel 134 to reinstate the normal time circulating step, thereby restoring the operation of the normal time circulating step shown in FIG. 7.

The cell culturing system 22 determines whether to end the culturing step (S40). The control unit 136 terminates the culturing step (S40) if the execution time period of the culturing step (S40) exceeds a predetermined threshold value. It should be noted that the final determination of the culturing step (S40) is not limited to such a technique, and for example, using the number of cells, which is calculated from the detection results of the culture parameter detection units 122, the culturing step (S40) may be terminated in the case that the number of cells becomes greater than or equal to a predetermined value.

In the releasing step (S50) after having performed the culturing step (S40), the release solution is supplied from the IC route 44A to thereby release the cells that were cultured (expanded) inside the bioreactor 20. In the collection step (S60) after having performed the releasing step (S50), by supplying the culture medium to the IC route 44A, the cells that were released in the releasing step (S50) are allowed to flow out from the bioreactor 20, and are guided into the collection bag 18E. At this time, the culture medium and the gas component are also supplied through the EC route 44B.

By the aforementioned step, the cell culturing system 22 can satisfactorily store the cells that were cultured in the bioreactor 20, in the collection bag 18E. In particular, in the cell culturing system 22, by providing a notification in the culturing step (S40) of the timing at which the enzyme sensor 124 should be replaced, the occurrence of an error in the detected concentration value due to deterioration of the enzyme sensor 124 is prevented. As a result, expansion of the cells can be stably managed, and further, the amount of the culture medium that is used can be reduced in accordance with the expansion of the cells.

Moreover, it should be noted that the present disclosure is not limited to the above-described embodiments, and various modifications can be adopted in accordance with the essence and gist of the present disclosure. For example, the cell culturing system 22 has been described as a configuration in which the flexible cassette main body 40 (e.g., the flow path cassette 10) is provided in the cell culturing kit 12. However, a configuration may be provided in which the cell culturing kit 12 is not equipped with such a flow path cassette 10, and a rigid flow path cassette 10 may be applied thereto.

Furthermore, the target of application to which the method of determining the lifespan of the enzyme sensors 124 according to the present disclosure is applied is not limited to being the cell culturing system 22, and such a method can be applied to various systems for measuring a substrate concentration using the enzyme sensors 124. For example, the method of determining the lifespan of the enzyme sensors 124 according to the present disclosure may be applied to a blood treatment system in which a blood treatment is carried out.

Figure 9:
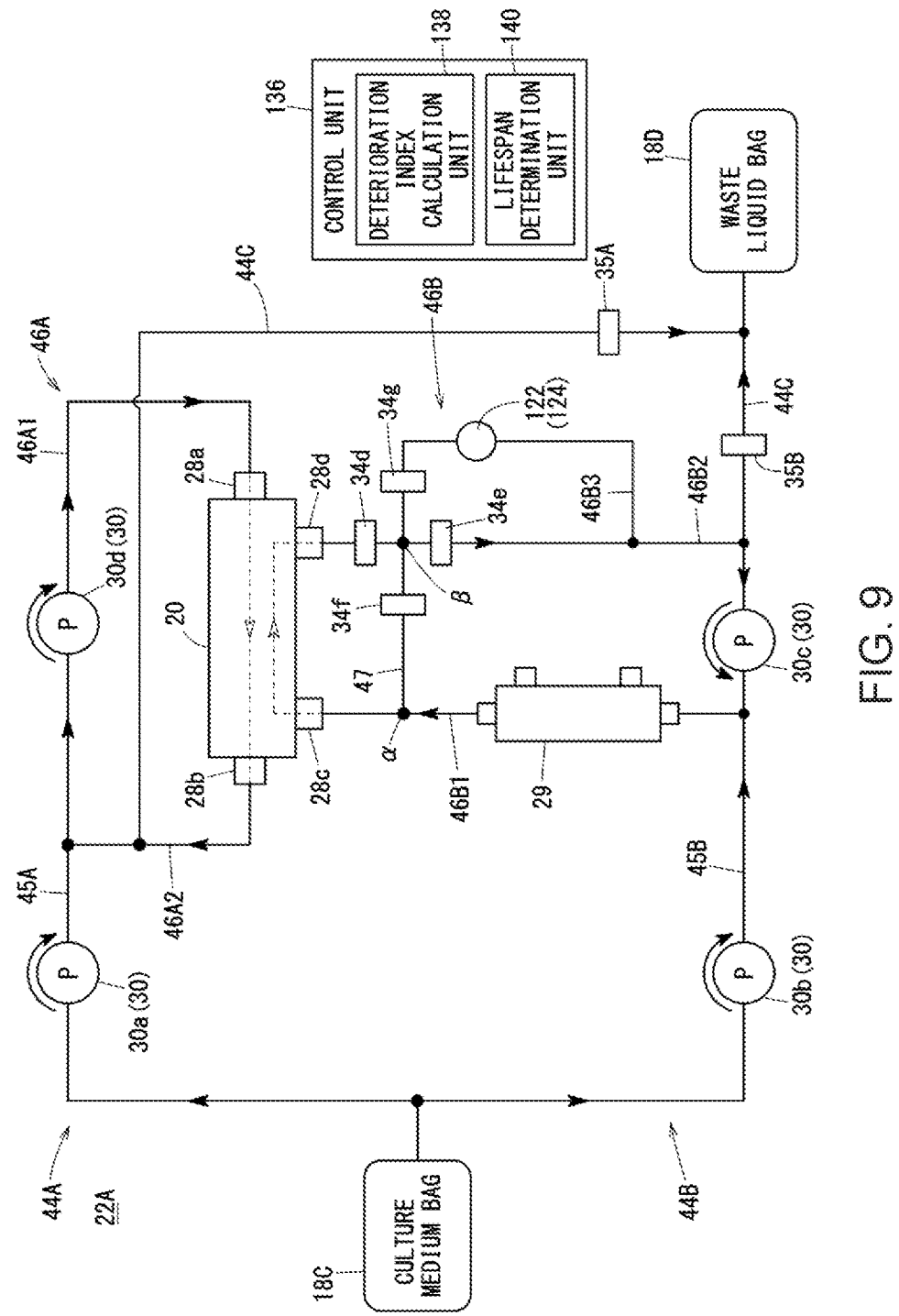
FIG. 9 is a schematic diagram showing liquid pathways of a cell culturing system according to at least one embodiment of the present disclosure.

As shown in FIG. 9, the cell culturing system 22A according to at least one embodiment of the present disclosure may differ from the cell culturing system 22 described above in that a branch pathway 46B3 is disposed in the EC outflow pathway 46B2, and the culture parameter detection unit 122 (e.g., the enzyme sensor 124) is arranged in the branch pathway 46B3. Moreover, the culture parameter detection unit 122 (e.g., the enzyme sensor 124) is not provided in the EC outflow pathway 46B2. In the cell culturing system 22A, the configurations of the IC route 44A (e.g., the IC supply circuit 45A, the IC circulation circuit 46A), and the EC supply circuit 45B are the same as those of the above-described cell culturing system 22, and detailed description of such features is omitted.

More specifically, one end of the branch pathway 46B3 is connected to the connection point beta where the EC outflow pathway 46B2 and the bypass pathway 47 are connected, and the other end of the branch pathway 46B3 is connected to the EC outflow pathway 46B2 on a more downstream side than the auxiliary clamp 34e. The branch pathway 46B3 may correspond to the tubes 16 as previously described above (not shown in FIG. 9).

At a position in close proximity to the connection point beta of the branch pathway 46B3, a switching clamp 34g is provided which is capable of opening and closing the branch pathway 46B3. The main clamp 34d, the auxiliary clamp 34e, and the sub-clamp 34f are provided at the same positions as previously described above. Further, the culture parameter detection unit 122 is disposed in series on a downstream side of the switching clamp 34g in the branch pathway 46B3.

One or more components and/or arrangements of the cell culturing system 22A may be configured similarly or in the same manner as described in conjunction with the cell culturing system 22 above. Next, a description will be given concerning replacement of the enzyme sensor 124 which is performed during the culturing step of the cell culturing system 22A.

In the cell culturing system 22A, in the normal time circulating step of the culturing process, the main clamp 34d, the auxiliary clamp 34e, and the switching clamp 34g are opened, while on the other hand, the sub-clamp 34f is closed by the control unit 136A. Consequently, in the EC route 44B, under a driving action of the third pump 30c, the culture medium flows from the EC inflow pathway 46B1 into the main space 26a of the bioreactor 20, and the culture medium flows out from the bioreactor 20 into the EC outflow pathway 46B2. The culture medium, in the course of flowing through the EC outflow pathway 46B2, passes through the parameter target detection units 110 (e.g., the culture parameter detection units 122) provided in the cassette main body 40. By opening the auxiliary clamp 34e and the switching clamp 34g, the culture medium flows through both the EC outflow pathway 46B2 and the branch pathway 46B3.

The amount of glucose or the amount of lactic acid of the culture medium flowing through the branch pathway 46B3 is detected by the culture parameter detection unit 122 (e.g., the enzyme sensor 124). The control unit 136A controls the supplied amount (e.g., a supply rate) of the culture medium based on the detection result. Moreover, a configuration may be provided in which, in the normal time circulating step, by closing the auxiliary clamp 34e, all of the culture medium flowing out from the bioreactor 20 is guided to the branch pathway 46B3.

When the enzyme sensor 124 is replaced, the control unit 136A opens the main clamp 34d and the auxiliary clamp 34e, while on the other hand, closes the sub-clamp 34f and the switching clamp 34g. Consequently, in the EC circulation circuit 46B, under the driving action of the third pump 30c, the culture medium that flows through the EC outflow pathway 46B2 does not flow through the branch pathway 46B3. Since the culture medium does not flow through the branch pathway 46B3, by the method that was described with reference to FIG. 5B, the deteriorated enzyme sensor 124 is replaced with a new enzyme sensor 124 using an aseptic joining device.

After the enzyme sensor 124 has been replaced, the control unit 136A continues to measure the concentration of the predetermined component, by opening the switching clamp 34g and allowing the culture medium to flow into the branch pathway 46B3. In this manner, in the cell culturing system 22A, the enzyme sensor 124 can be replaced without stopping circulation of the culture medium in the EC circulation circuit 46B.

Figure 10:
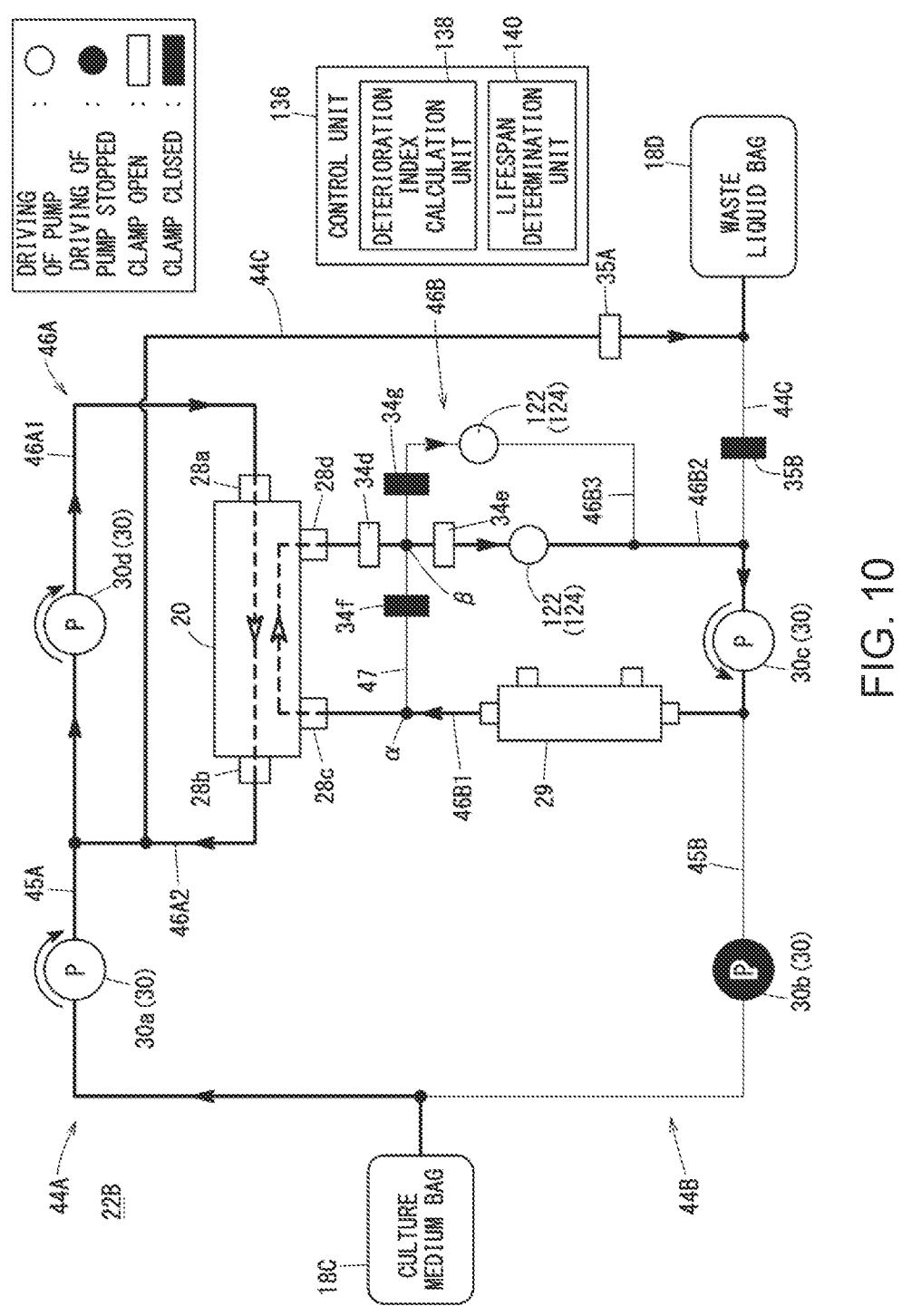
FIG. 10 is a schematic diagram showing liquid pathways of a cell culturing system according to at least one embodiment of the present disclosure.

As shown in FIG. 10, the cell culturing system 22B may differ from the cell culturing system 22A described above in that culture parameter detection units 122 (e.g., the enzyme sensors 124) are arranged respectively in the EC outflow pathway 46B2 and the branch pathway 46B3. In the cell culturing system 22B, the configurations of the EC outflow pathway 46B2 and the branch pathway 46B3, along with the auxiliary clamp 34e and the switching clamp 34g that are provided therein, are the same as those of the cell culturing system 22A, and detailed description of such features is omitted.

In the cell culturing system 22B, a configuration is provided in which the enzyme sensors 124 are installed in parallel in the EC outflow pathway 46B2 and the branch pathway 46B3. At the start of the culturing step (S40), only one of the enzyme sensors 124 is used, and after such an enzyme sensor 124 has become deteriorated, it is possible to switch to the other enzyme sensor 124.

One or more components and/or arrangements of the cell culturing system 22B may be configured similarly or in the same manner as described in conjunction with the cell culturing systems 22, 22A above. Next, a description will be given concerning a switching operation of the enzyme sensors 124 performed during the culturing step (S40) of the cell culturing system 22B.

In the cell culturing system 22B, in the normal time circulating step of the culturing process, the main clamp 34d and the auxiliary clamp 34e are opened, while on the other hand, the switching clamp 34g and the sub-clamp 34f are closed by the control unit 136B. Consequently, the culture medium flows through the EC outflow pathway 46B2, and does not flow into the branch pathway 46B3. The enzyme sensor 124 of the branch pathway 46B3 is kept in a state of not touching the predetermined component of the culture medium, and deterioration of the enzyme sensor 124 can be prevented.

Figure 11:
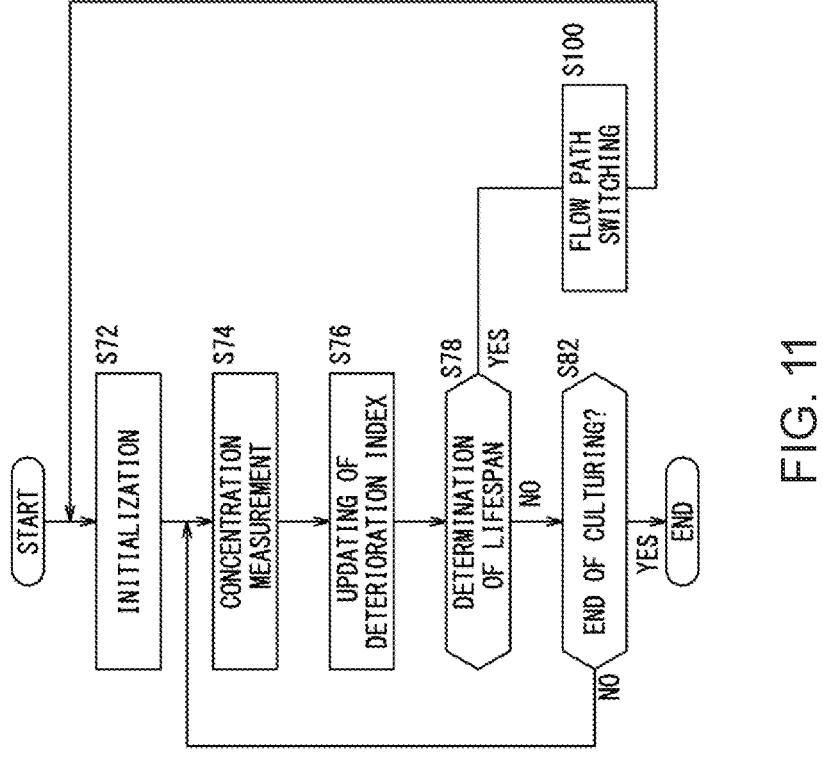
FIG. 11 is a flowchart showing a method of determining a lifespan of the enzyme sensor of the cell culturing system of FIG. 10, and a switching operation of the enzyme sensor according to at least one embodiment of the present disclosure.

Further, during execution of the normal time circulating step, the control unit 136B performs a switching determination process of the enzyme sensors 124, in accordance with steps S72 to S100 shown in FIG. 11. During the switching determination process shown in FIG. 11, the steps from initialization (step S72) to determination of the lifespan (step S78), as well as determination of the end of culturing (step S82) are the same as in the lifespan determination process of FIG. 6B, and therefore, description of these steps is omitted.

Figure 12:
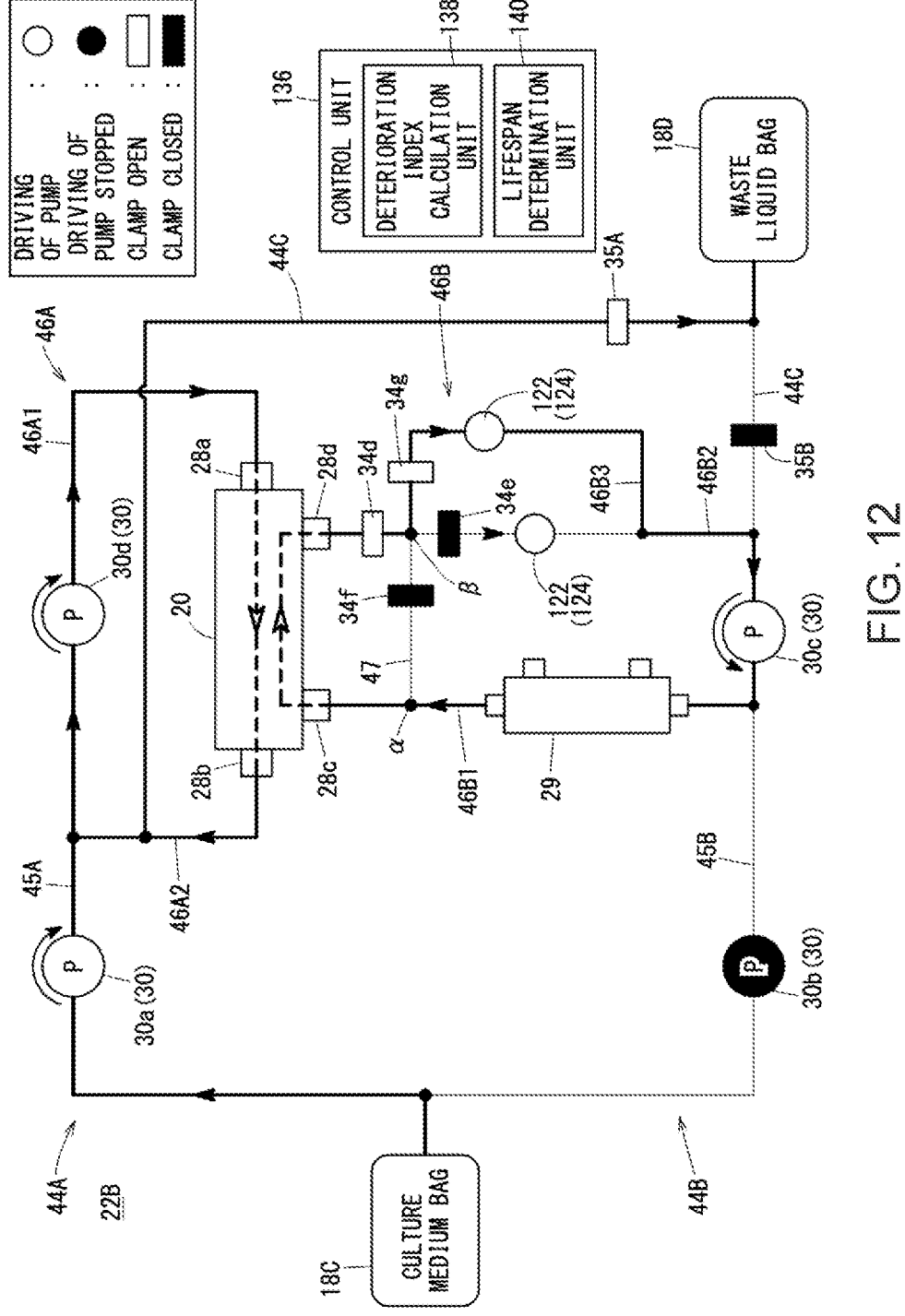
FIG. 12 is a schematic diagram showing liquid pathways of the cell culturing system shown in FIG. 10 according to at least one embodiment of the present disclosure.

In the lifespan determination process (step S78), in the case that the lifespan determination unit 140 has detected that the deterioration index of the enzyme sensor 124 exceeds the threshold value, a sensor flow path switching process (step S100) is performed. In the sensor flow path switching process (step S100), as shown in FIG. 12, the control unit 136B closes the auxiliary clamp 34e and opens the switching clamp 34g, thereby allowing the culture medium to flow into the branch pathway 46B3. Consequently, by the enzyme sensor 124 that is not deteriorated, it is possible to continue measuring the concentration of the predetermined component of the culture medium.

Moreover, along with closing of the auxiliary clamp 34e, the culture medium does not flow into the EC outflow pathway 46B2. Therefore, while measurement of the concentration is being carried out by the enzyme sensor 124 disposed on the branch pathway 46B3, replacement of the enzyme sensor 124 disposed on the EC outflow pathway 46B2 may be performed so as to prepare for a subsequent sensor switching operation.

Thereafter, in order to determine the lifespan of the new enzyme sensor 124 (in the branch pathway 46B3), the process transitions to step S72 to thereby determine the lifespan of the enzyme sensor 124. In the foregoing manner, according to the cell culturing system 22B of the present embodiment, measurement of the concentration of the culture medium can be continued without reconnecting the enzyme sensor 124, resulting in saved labor costs.

In the above description, although an example case has been described in which one branch pathway 46B3 is disposed in parallel with the EC outflow pathway 46B2, the present embodiment is not limited to this feature. By providing a plurality of branch pathways 46B3 equipped with enzyme sensors 124, the enzyme sensors 124 may be prepared for undergoing deterioration.

Technical concepts and effects that can be determined from the above-described embodiments will be described below.

A first aspect of the present disclosure is characterized by the cell culturing system 22, 22A, 22B including the enzyme sensor 124 that detects the concentration of the predetermined component (substrate) of the culture medium used for culturing of cells, the sensor flow path (EC outflow pathway 46B2) in which the enzyme sensor 124 is disposed, and the bioreactor 20 that performs culturing of the cells while causing the culture medium to flow through the sensor flow path, the cell culturing system 22, 22A, 22B further including the deterioration index calculation unit 138 that determines the deterioration index of the enzyme sensor 124, based on a detected concentration value of the enzyme sensor 124, and the detection period during which the detected concentration value is detected, and the lifespan determination unit 140 that detects whether or not the integrated value of the deterioration index has reached the threshold value, and thereby determines the lifespan of the enzyme sensor 124.

In accordance with the above-described configuration, even in the case that the concentration of the predetermined component (substrate) of the culture medium fluctuates greatly between an initial stage of culturing and a final stage of culturing, it is possible to determine the lifespan of the enzyme sensor 124 by reflecting on the progression in deterioration due to an increase in the substrate concentration.

In the cell culturing system 22, 22A, 22B according to the above-described aspect, the enzyme sensor 124 may be a sensor configured to detect a glucose concentration or a lactic acid concentration. In accordance with this feature, the enzyme sensor 124 which is superior in selectivity can be used for measuring a glucose concentration or a lactic acid concentration, and management of the culturing operation of the cell culturing system 22, 22A and 22B can be carried out more appropriately.

In the cell culturing system 22, 22A, 22B according to the above-described aspect, a configuration may be provided including the touch panel 134 (display operation unit) which displays the concentration of the predetermined component, wherein, when the lifespan determination unit 140 determines that the end of the lifespan of the enzyme sensor 124 has been reached, the touch panel 134 performs a display to prompt replacement of the enzyme sensor 124. In accordance with this feature, replacement of the enzyme sensor 124 can be performed at an appropriate timing, without being misled by fluctuations in the detected value.

In the cell culturing system 22A according to the above described aspect, a configuration may be provided which is equipped with the EC outflow pathway 46B2 disposed alongside the branch pathway 46B3 (sensor flow path), and the switching clamp 34*g* that is capable of blocking communication between the bioreactor 20 and the branch pathway 46B3, wherein the control unit 136 closes the switching clamp 34*g* when the enzyme sensor 124 is replaced. In accordance with such a configuration, the enzyme sensor 124 can be replaced without stopping circulation of the culture medium.

In the cell culturing system 22B according to the above described aspect, there may further be provided a plurality of the sensor flow paths (the EC outflow pathway 46B2 and the branch pathway 46B3) in which enzyme sensors 124 are provided respectively, and which are arranged alongside one another in parallel. The cell culturing system may further include the clamps (the auxiliary clamp 34*e* and the switching clamp 34*g*) that switch and connect one of the plurality of the sensor flow paths to the bioreactor 20, and the control unit 136B that operates the clamps (the auxiliary clamp 34*e* and the switching clamp 34*g*), and switches and connects another one of the sensor flow paths (the EC outflow pathway 46B2 and the branch pathway 46B3), when the lifespan determination unit 140 detects that the deterioration index of one of the enzyme sensors 124 has reached the threshold value. In accordance with such a configuration, since the enzyme sensor 124 can be switched to a new enzyme sensor 124 without performing a replacement operation, labor costs can be reduced.

A second aspect of the present disclosure is characterized by the method of determining the lifespan of the enzyme sensor 124 in the cell culturing system 22, 22A, 22B in which cells are cultured while detecting the concentration of the predetermined component of the culture medium using the enzyme sensor 124, the method of determining the lifespan of the enzyme sensor 124 including the step of detecting (S74), by the control unit 136, the detected concentration value of the enzyme sensor 124, and the detection period during which the detected concentration value is detected, the deterioration index detection step (S76) of determining, in the deterioration index calculation unit 138, the integrated value of the deterioration index of the enzyme sensor 124, based on the detected concentration value of the enzyme sensor 124 and the detection period, and the lifespan determination step (S78) of determining, by the lifespan determination unit 140, whether or not the end of the lifespan has been reached based on whether the deterioration index has reached the threshold value. In accordance with the above-described method of determining the lifespan, even in the case that the concentration of the predetermined component (substrate) of the culture medium fluctuates greatly between an initial stage of culturing and a final stage of culturing, it is possible to determine the lifespan of the enzyme sensor 124 by examining the progression in deterioration due to an increase in the substrate concentration.

A third aspect of the present disclosure is characterized by the sensor kit used in the cell culturing system 22, 22A, 22*b*, the sensor kit including the enzyme sensor 124 that detects the concentration of the predetermined component of a culture medium used for culturing of cells, and the tube 125 (the sensor flow path) extended from the one end and the other end of the enzyme sensor 124, wherein the tube 125 (the sensor flow path) is made up from a thermoplastic tube both ends of which are closed by the fusion bonded portions 125*a*, and which is capable of being aseptically joined to the flow path (the second IC tube 16G and the second EC tube 16I) through which the culture medium of the cell culturing system 22, 22A, 22B flows, and the enzyme sensor 124 is configured to detect the concentration of the predetermined component within the culture medium, and transmit a detected value to the cell culturing system 22, 22A, 22B.

According to the above-described sensor kit, since a replacement operation of the enzyme sensor 124 can be easily carried out simply by changing the connection of the tube 125, labor costs can be reduced in the operation of managing the cell culturing system 22, 22A, 22B.

Figure 13:
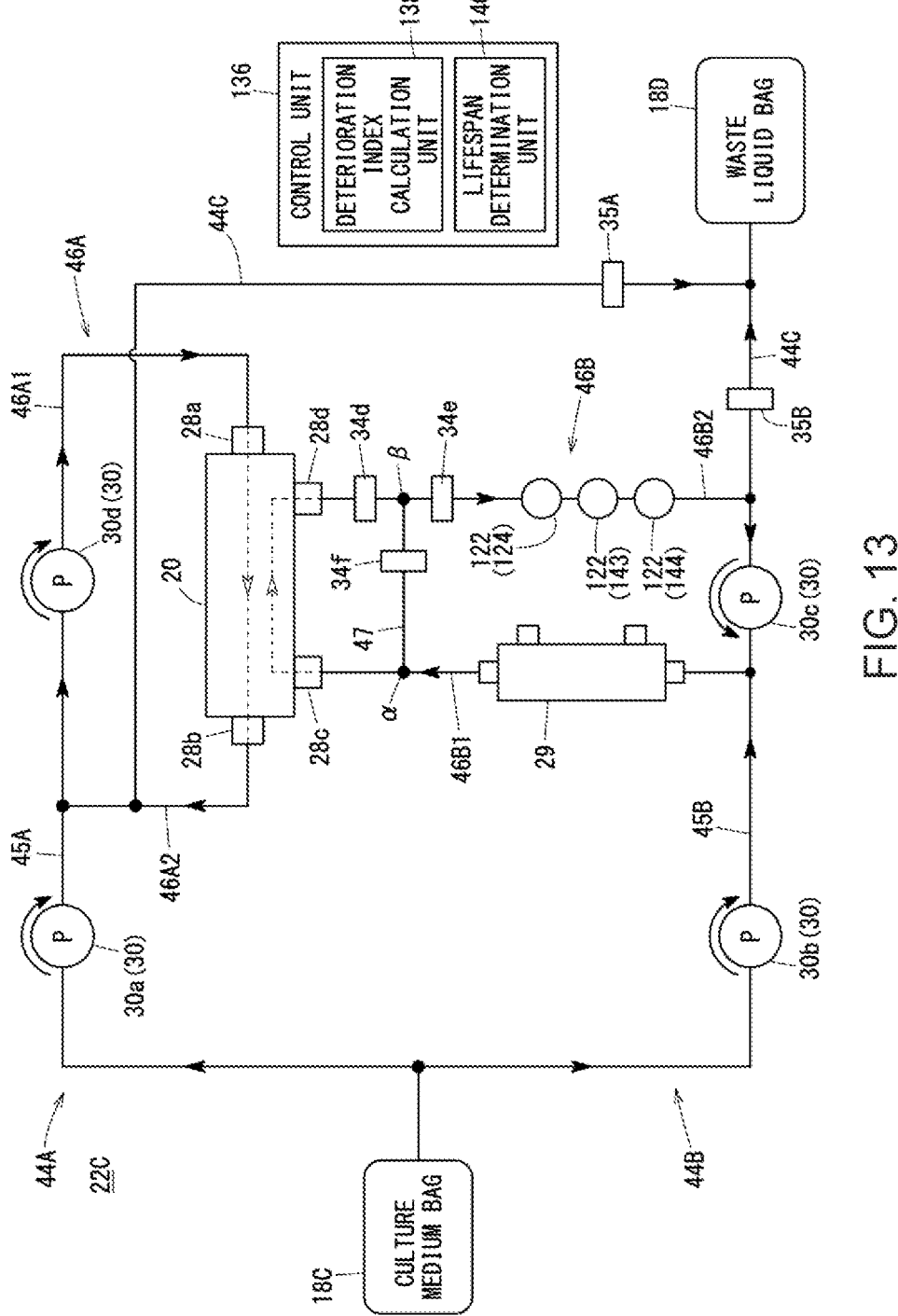
FIG. 13 is a schematic diagram showing liquid pathways of a cell culturing system according to at least one embodiment of the present disclosure.

As shown in FIG. 13, the cell culturing system 22C may differ from the cell culturing system 22 shown in FIG. 4 in that a temperature sensor 144 and a pH sensor 143 are added as culture parameter detection units 122 to the EC circulation circuit 46B. Further, in the cell culturing system 22C, the influence of the temperature and the pH of the EC culture medium is reflected in the calculation of the deterioration index of the deterioration index calculation unit 138A. Moreover, in the cell culturing system 22C of the present embodiment, configurations which are the same as those of the cell culturing system 22 of FIG. 4 are designated by the same reference numerals, and detailed description of such features is omitted.

The temperature sensor 144 is disposed midway along the EC outflow pathway 46B2, and is a sensor that detects the temperature of the EC culture medium flowing through the EC circulation circuit 46B, and outputs temperature data to the control unit 136. The position where the temperature sensor 144 is installed is not limited to the EC outflow pathway 46B2, and the sensor may be disposed at any arbitrary position of the EC circulation circuit 46B.

The pH sensor 143 is disposed midway along the EC outflow pathway 46B2, and is a sensor that detects the pH (hydrogen ion concentration) of the EC culture medium flowing through the EC circulation circuit 46B, and outputs pH data to the control unit 136. As the pH sensor 143, a commercially available pH measuring device using a glass electrode can be used. The position where the pH sensor 143 is installed is not limited to the EC outflow pathway 46B2, and the sensor may be disposed at any arbitrary position of the EC circulation circuit 46B.

Figure 14:
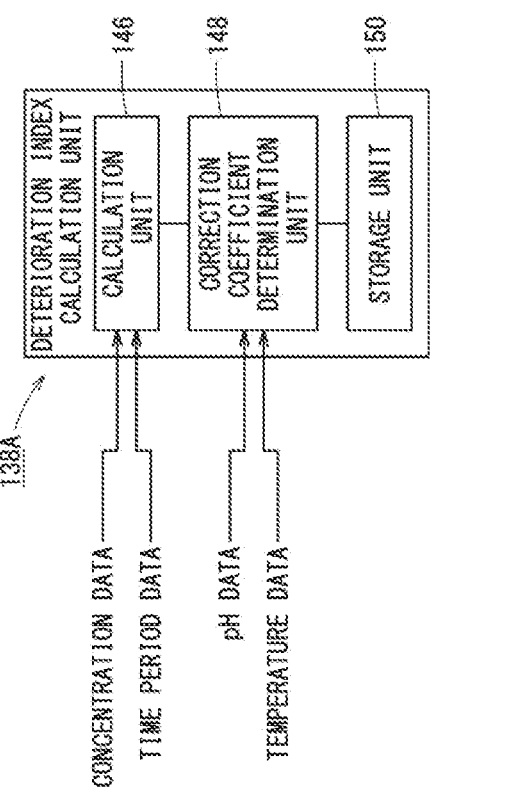
FIG. 14 is a block diagram of a deterioration index calculation unit of the cell culturing system shown in FIG. 13 according to at least one embodiment of the present disclosure.

As shown in FIG. 14, the deterioration index calculation unit 138A of the present embodiment is equipped with a calculation unit 146, a correction coefficient determination unit 148, and a storage unit 150. The calculation unit 146 calculates the deterioration index on the basis of concentration data which is a detected value of the enzyme sensor 124, a pH correction coefficient, and a temperature correction coefficient.

The correction coefficient determination unit 148 determines the pH correction coefficient based on the pH data of the culture medium detected by the pH sensor 143. Further, the correction coefficient determination unit 148 determines the temperature correction coefficient based on the temperature data of the culture medium detected by the temperature sensor 144.

Figure 15A:
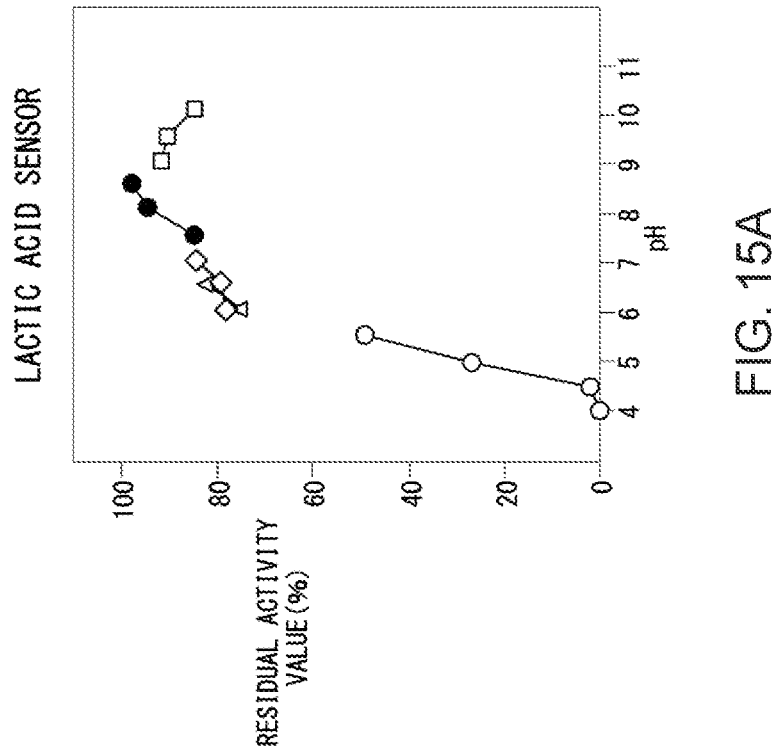
FIG. 15A is a graph showing an enzyme stability of a glucose sensor with respect to pH according to at least one embodiment of the present disclosure.
Figure 15B:
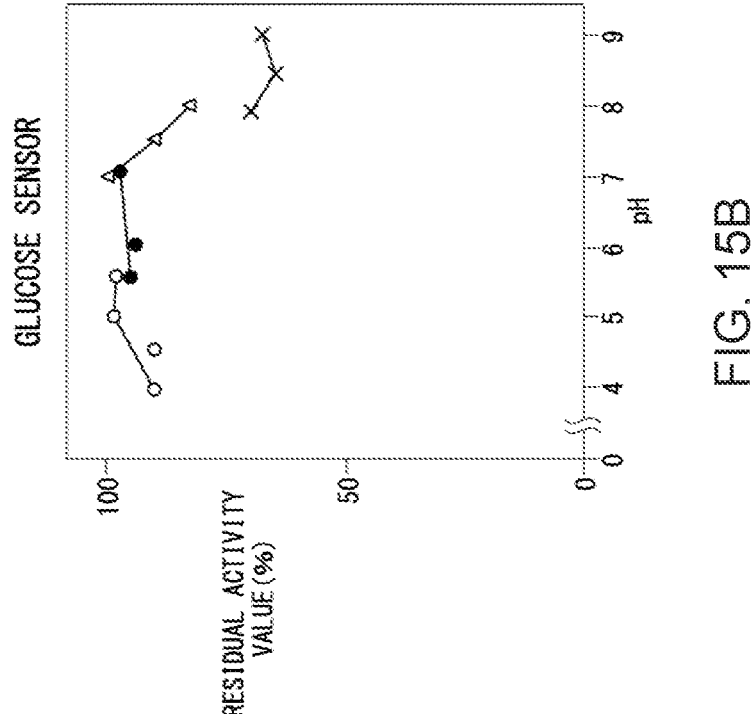
FIG. 15B is a graph showing an enzyme stability of a glucose sensor with respect to pH according to at least one embodiment of the present disclosure.

In FIGS. 15A and 15B, the pH of the culture medium is indicated on the horizontal axis, and the measurement result of the enzyme activity (residual activity value) of the enzyme sensor 124 after being placed in contact with the culture medium for a certain period of time is indicated on the vertical axis, and an enzyme stability with respect to the pH is shown. FIG. 15A shows a residual stability of the enzyme of the enzyme sensor 124 (e.g., a lactic acid sensor) that detects the lactic acid concentration. As illustrated, the enzyme of the lactic acid sensor tends to be less stable when the pH of the culture medium is less than 8, and deterioration progresses more rapidly as the pH value becomes lower. Accordingly, it can be understood that the degree of progression in the deterioration of the enzyme sensor 124 (e.g., a lactic acid sensor) has a value depending on the pH.

Further, as shown in FIG. 15B, in the case of an enzyme sensor 124 (e.g., a glucose sensor) that detects the glucose concentration, the stability of the enzyme decreases when the pH lies outside of the range of 5 to 8. The degree of progression in the deterioration of the enzyme of the glucose sensor also exhibits a change that depends on the pH. In the present embodiment, the degree of progression in the deterioration of the enzyme sensor 124, such as the lactic acid sensor and the glucose sensor, in accordance with pH is reflected as a pH correction coefficient in the calculation of the deterioration index.

A pH correction coefficient map, which indicates a relationship between the pH value of the culture medium and the pH correction coefficient of the enzyme sensor 124, is stored in the storage unit 150 of the deterioration index calculation unit 138A shown in FIG. 14. The pH correction coefficient is a numerical value having a value ranging, for example, from 0.1 to 2, and is a value which is obtained experimentally, so that the value becomes greater as the degree of progression in the deterioration (e.g., deterioration rate) of the enzyme sensor 124 becomes more rapid. The correction coefficient determination unit 148 determines the pH correction coefficient by referring to the pH correction coefficient map in the storage unit 150, and based on the pH data of the culture medium detected by the pH sensor 143.

Figure 16A:
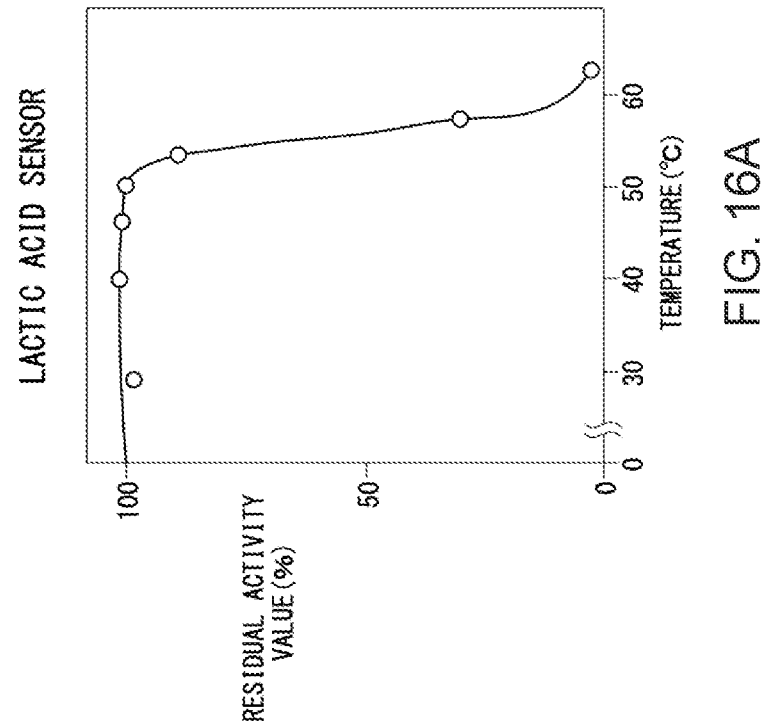
FIG. 16A is a graph showing an enzyme stability with respect to temperature of a lactic acid sensor according to at least one embodiment of the present disclosure.
Figure 16B:
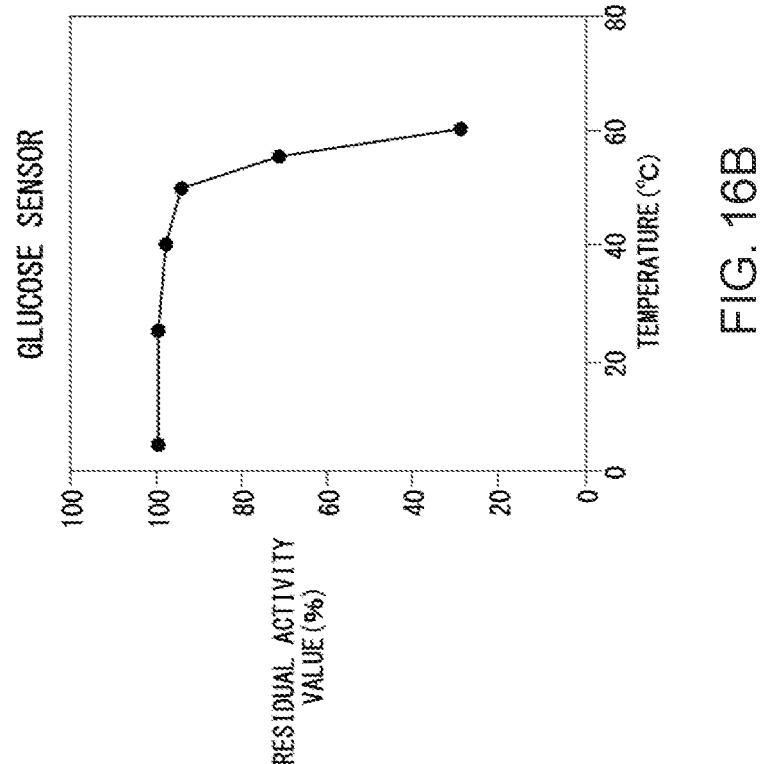
FIG. 16B is a graph showing an enzyme stability with respect to temperature of the glucose sensor according to at least one embodiment of the present disclosure.

On the other hand, the stability of the enzyme sensor 124 also changes depending on the temperature of the culture medium. In FIGS. 16A and 16B, the temperature of the culture medium is indicated on the horizontal axis, and the residual activity value of the enzyme used in the enzyme sensor 124 after a certain period of time has elapsed is indicated on the vertical axis, and the enzyme stability is shown. As shown in FIG. 16A, in the case of the enzyme sensor 124 (e.g., a lactic acid sensor), a change in the residual activity (e.g., a stability) in accordance with the temperature of the culture medium is exhibited, and it is understood that the deterioration progresses more rapidly in particular when the temperature exceeds 50° C. Further, as shown in FIG. 16B, it can be understood that, even in the case of the enzyme sensor 124 (e.g., a glucose sensor), the deterioration progresses more rapidly when the temperature of the culture medium exceeds 50° C.

A temperature correction coefficient map, which indicates a relationship between the temperature of the culture medium and the temperature correction coefficient of the enzyme sensor 124, is stored in the storage unit 150 shown in FIG. 14. The temperature correction coefficient is a numerical value having a value ranging, for example, from 0.1 to 2, and a value is used which is obtained experimentally, so that the value becomes greater as the degree of progression in the deterioration (deterioration rate) of the enzyme sensor 124 becomes more rapid. The correction coefficient determination unit 148 determines the temperature correction coefficient by referring to the temperature correction coefficient map in the storage unit 150, and based on the temperature data which is the detected value of the temperature sensor 144.

In the calculation unit 146, the deterioration index calculation unit 138A calculates the deterioration index by the following formula, based on the concentration data which is the detection value of the enzyme sensor 124, the pH correction coefficient, and the temperature correction coefficient.

Deterioration Index=(Actual Time Period×pH Correction Coefficient×Temperature Correction Coefficient)×Concentration Data In the above formula, the actual time period can be the difference between a previous time of measurement of the concentration, the pH, and the temperature, and a current time of measurement of the concentration, the pH, and the temperature.

The cell culturing system 22C according to the present embodiment is configured in the manner described above, and performs similar or the same operations as the operations described with reference to FIGS. 6A and 6B. However, in updating the deterioration index (step S76) of FIG. 6B, the deterioration index calculation unit 138A calculates the deterioration index on the basis of the pH correction coefficient and the temperature correction coefficient, and then carries out updating of the deterioration index.

More specifically, the deterioration index calculation unit 138A acquires the pH data in the correction coefficient determination unit 148, and by referring to the pH correction coefficient map of the storage unit 150, determines the pH correction coefficient in accordance with the pH value. Further, the correction coefficient determination unit 148 acquires the temperature data, and by referring to the temperature correction coefficient map of the storage unit 150, determines the temperature correction coefficient. Thereafter, in the calculation unit 146, the deterioration index calculation unit 138A multiplies the time period, the pH correction coefficient, the temperature correction coefficient, and the concentration data, and thereby calculates the deterioration index. By adding the deterioration index to the integrated value of past deterioration indexes, the integrated value of the deterioration index is updated.

In the cell culturing system 22C of the present embodiment, upon determining the lifespan of the enzyme sensor 124 in the manner described above, the lifespan of the enzyme sensor 124 is determined by taking into consideration the pH and the temperature of the culture medium, in addition to the concentration and the detection period thereof. Owing to this feature, the lifespan of the enzyme sensor 124 can be determined more accurately.

Further, on the basis of the present embodiment, the sensor kit may be configured as a sensor kit in which the enzyme sensor 124 is provided, together with the pH sensor 143 that detects the hydrogen ion concentration (pH) of the culture medium. In accordance with such a configuration, the replacement operation of the pH sensor 143 can be carried out together with that of the enzyme sensor 124, and a savings of labor is possible in the operation of managing the cell culturing system 22, 22A, 22B.

Although embodiments of the present disclosure have been described above, the present disclosure is not limited to the above-described embodiments. It goes without saying that various modifications can be adopted therein without departing from the scope of the disclosure.

What is claimed is:

1. A cell culturing system, comprising:

an enzyme sensor configured to detect a concentration of a predetermined component of a culture medium used for culturing of cells;

a sensor flow path in which the enzyme sensor is disposed;

a bioreactor configured to perform culturing of the cells while causing the culture medium to flow through the sensor flow path;

a processor; and memory including a program, that when executed by the processor causes the processor to:

determine a concentration value of the predetermined component of the culture medium based on output of the enzyme sensor;

determine a deterioration index of the enzyme sensor by multiplying the concentration value of the predetermined component of the culture medium by a detection period during which the enzyme sensor senses the concentration value; and determine a lifespan of the enzyme sensor based on whether the deterioration index has reached a threshold value.

2. The cell culturing system of claim 1, wherein the enzyme sensor is configured to detect a glucose concentration or a lactic acid concentration.

3. The cell culturing system of claim 2, further comprising:

a display configured to display the concentration of the predetermined component, wherein, when the processor determines that an end of the lifespan of the enzyme sensor has been reached, the display displays a prompt to replace the enzyme sensor.

4. The cell culturing system of claim 1, further comprising:

a flow path disposed in parallel with the sensor flow path;

a switching clamp configured to block the sensor flow path, wherein the switching clamp is controlled to close when replacing the enzyme sensor.

5. The cell culturing system of claim 1, further comprising a second sensor flow path arranged alongside the sensor flow path in parallel, and wherein the cell culturing system further comprises:

a clamp configured to switch and connect one of the sensor flow path or the second sensor flow path to the bioreactor, wherein when the processor determines that the deterioration index of the enzyme sensor or a deterioration index of a second enzyme sensor disposed in the second sensor flow path has reached the threshold value, the processor operates the clamp to switch and connect a third sensor flow path to the bioreactor.

6. The cell culturing system of claim 1, further comprising:

a pH sensor configured to detect a hydrogen ion concentration (pH) of the culture medium, wherein the program, when executed by the processor, causes the processor to:

determine a pH correction coefficient based on a pH correction coefficient map and based on the hydrogen ion concentration of the culture medium detected by the pH sensor, the pH correction coefficient map indicating a relationship between the hydrogen ion concentration and a deterioration rate of the enzyme sensor; and determine the deterioration index of the enzyme sensor further based on the pH correction coefficient.

7. The cell culturing system of claim 1, further comprising:

a temperature sensor configured to detect a temperature of the culture medium, wherein the program, when executed by the processor, causes the processor to:

determine a temperature correction coefficient based on a temperature correction coefficient map and based on the temperature of the culture medium detected by the temperature sensor, the temperature correction coefficient map indicating a relationship between the temperature and a deterioration rate of the enzyme sensor; and determine the deterioration index of the enzyme sensor further based on the temperature correction coefficient.

8. A sensor kit, comprising:

an enzyme sensor configured to detect a concentration of a predetermined component of a culture medium used for culturing of cells; and a sensor flow path extended from a first end and a second end of the enzyme sensor, wherein the sensor flow path is made up from a thermoplastic tube that is closed at the first end and the second end and that is configured to be aseptically joined to a flow path through which the culture medium of a cell culturing system flows;

a processor; and memory including a program, that when executed by the processor causes the processor to:

determine a concentration value of the predetermined component of the culture medium based on output of the enzyme sensor;

determine a deterioration index of the enzyme sensor by multiplying the concentration value of the predetermined component of the culture medium by a detection period during which the enzyme sensor detects the concentration value; and determine a lifespan of the enzyme sensor based on whether the deterioration index has reached a threshold value.

9. The sensor kit of claim 8, further comprising a pH sensor configured to detect a hydrogen ion concentration (pH) of the culture medium.

10. The sensor kit of claim 8, wherein the enzyme sensor is configured to detect a glucose concentration or a lactic acid concentration.

11. The sensor kit of claim 8, further comprising:

a temperature sensor configured to detect a temperature of the culture medium.

12. The sensor kit of claim 8, wherein the sensor flow path is configured to connect with a bioreactor that performs culturing of the cells while causing the culture medium to flow through the sensor flow path.

13. The sensor kit of claim 8, wherein a display receives the concentration value of the predetermined component of the culture medium and displays the concentration value.

14. The sensor kit of claim 13, wherein the display further renders, when the deterioration index has reached the threshold value, a prompt indicating that the enzyme sensor should be replaced.

* * * * *